(12) United States Patent
Kirby et al.

(10) Patent No.: US 10,370,716 B2
(45) Date of Patent: Aug. 6, 2019

(54) METHODS OF DIAGNOSING AND TREATING MEDULLARY CYSTIC KIDNEY DISEASE

(71) Applicants: THE BROAD INSTITUTE, INC., Cambridge, MA (US); THE GENERAL HOSPITAL CORPORATION, Boston, MA (US); Instituto Carlos Slim de la Salud, A.C., Mexico City (MX)

(72) Inventors: Andrew Kirby, Wellesley, MA (US); Andreas Gnirke, Wellesley, MA (US); Brendan Blumenstiel, Arlington, MA (US); Matthew Defelice, Salem, MA (US); Mark Daly, Arlington, MA (US)

(73) Assignees: THE BROAD INSTITUTE, INC., Cambridge, MA (US); THE GENERAL HOSPITAL CORPORATION, Boston, MA (US); INSTITUTO CARLOS SLIM DE LA SALUD, A.C., Mexico City (MX)

( * ) Notice: Subject to any disclaimer, the term of this patent is extended or adjusted under 35 U.S.C. 154(b) by 8 days.

(21) Appl. No.: 14/618,525

(22) Filed: Feb. 10, 2015

(65) Prior Publication Data
US 2015/0252423 A1 Sep. 10, 2015

Related U.S. Application Data

(63) Continuation-in-part of application No. PCT/US2013/054301, filed on Aug. 9, 2013.

(60) Provisional application No. 61/681,937, filed on Aug. 10, 2012.

(51) Int. Cl.
C12Q 1/6883 (2018.01)
C12N 15/113 (2010.01)

(52) U.S. Cl.
CPC ........ *C12Q 1/6883* (2013.01); *C12N 15/1138* (2013.01); *C12Q 2600/118* (2013.01); *C12Q 2600/156* (2013.01)

(58) Field of Classification Search
CPC ............ C12Q 1/6883; C12Q 2600/118; C12Q 2600/156
See application file for complete search history.

(56) References Cited

PUBLICATIONS

Braasch et al. (Biochem. 2002; vol. 41, pp. 4503-4510).*
Gewirtz et al. (PNAS 1996, vol. 93, pp. 3161-3163).*
Agrawal (TIBTECH 1996, vol. 14, pp. 376-387).*
Branch et al. (TIBS, Feb. 1998; pp. 45-50).*
International Search Report for International application No. PCT/US2013/054301 dated Nov. 27, 2013.
K Christodoulou: "Chromosome 1 localization of a gene for autosomal dominant medullary cystic kidney disease", Human Molecular Genetics, vol. 7, No. 5, May 1, 1998 (May 1, 1998), pp. 905-911.
Matthias T F Wolf et al: "Medullary cystic kidney disease type 1: mutational analysis in 37 genes based on haplotype sharing", Human Genetics, Springer, Berlin, DE, vol. 119, No. 6, Apr. 26, 2006.
Andrew Kirby et al: "Mutations causing medullary cystic kidney disease type 1 lie in a large VNTR in MUC1 missed by massively parallel sequencing", Nature Genetics, vol. 45, No. 3, Feb. 10, 2013 (2813-82-10), pp. 299-303.
Kiser R L et al: "Medullary cystic kidney disease type 1 in a large Native-American kindred", American Journal of Kidney Diseases, W.B. Saunders, Philadelpphia, PA, US, vol. 44, No. 4, Oct. 1, 2004 (Oct. 1, 2004), pp. 611-617.
Joanna C. Fowler et al: "Hypervariability of the membrane-associated mucin and cancer marker MUC1", Human Genetics, vol. 113, No. 6, Nov. 1, 2003 (2883-11-81), pp. 473-479.
Melissa Brayman et al: "Reproductive Biology and Endocrinology MUC1: A multifunctional cell surface component of reproductive tissue epithelia".Jan. 7, 2004 (Jan. 7, 2004).
International Preliminary Report on Patentability and Written Opinion of the International Searching Authority dated Feb. 10, 2015, which issued during prosecution of International Application No. PCT/US2013/054301.

* cited by examiner

*Primary Examiner* — J. E. Angell
(74) *Attorney, Agent, or Firm* — Burns & Levinson LLP; Richard B. Emmons; Christopher R. Cowles

(57) ABSTRACT

The present invention features a highly sensitive assay for detecting frameshift mutations for high throughput use. Also provided herein are methods for diagnosing or determining a predisposition for developing medullary cystic kidney disease type 1 (MCKD1) in a subject by detecting a frameshift mutation in the GC-rich variable number of tandem repeats (VNTR) sequence of the mucin 1 gene (MUC-1).

18 Claims, 11 Drawing Sheets
Specification includes a Sequence Listing.

Figure 1

```
AAGGAGACTTCGGCTACCCAGAGAAGTTCAGTGCCCAGCTCTACTGAGAAGAATGCTGTG  1   SEQ ID NO:15
AGTATGACCAGCAGCGTACTCTCCAGCCACAGCCCCGGTTCAGGCTCCTCCACCACTCAG  2   SEQ ID NO:16
GGACAGGATGTCACTCTGGCCCCGGCCACGGAACCAGCTTCAGGTTCAGCTGCCACCTGG  3   SEQ ID NO:17
GGACAGGATGTCACCTCGGTCCCAGTCACCAGGCCAGCCCTGGGCTCCACCACCCCGCCA  4   SEQ ID NO:18
GGACAGGATGTCACCTCGGTCCCAGTCACCAGGCCAGCCCTGGGCTCCACCACCCCaCCA  4'  SEQ ID NO:19
GCCCACGATGTCACCTCAGCCCCGGACAACAAGCCAGCCCCGGGCTCCACCGCCCCCCCA  5   SEQ ID NO:20

GCCCACGGTGTCACCTCGGCCCCGGACACCAGGCCGGCCCCGGGCTCCACCGCCCCCCCA  X   SEQ ID NO:21
GCCCACGGTGTCACCTCGGCCCCGGAgAgCAGGCCGGCCCCGGGCTCCACCGCgCCCgCA  A   SEQ ID NO:22
GCCCACGGTGTCACCTCGGCCCCGGAgAgCAGGCCGGCCCCGGGCTCCACCGCCCCCCCA  B   SEQ ID NO:23
GCCCACGGTGTCACCTCGGCCCCGGACACCAGGCCGGCCCCGGGCTCCACCGCCCCCCaA  C   SEQ ID NO:24
GCCCACGGTGTCACCTCGGCCCCGGACACCAGGCCcGCCCCGGGCTCCACCGCCCCCCCA  D   SEQ ID NO:25
GCCCACGGTGTCACCTCGGCCCCGGACACCAGGCCcGCCCCGGGCTCCACCGCgCCCgCA  E   SEQ ID NO:26
GCCCACGGTGTCACCTCGGCCCCGGACACCAGGCCGGCCCCGGGCTCCACCGCCCCCaCA  F   SEQ ID NO:27
GCCCACGGTGTCACCTCGGCCCCGGACACCAGGCCGGCCCCGGGCTCCACCGCgCCCgCA  G   SEQ ID NO:28
GCCCACGGTGTCACCTCGGCCCCGGACACCAGGCCGGCCCCGGGCTCCACCGCCgCCCCA  H   SEQ ID NO:29
GCCCACGGTGTCACCTCGGCCCCGGACACCAGGCCGGCCCCGGGCTCCACCGCgCCCCCA  I   SEQ ID NO:30
GCCCACGGTGTCACCTCGGCaCCGGAgAgCAGGCCGGCCCCGGGCTCCACCGCgCCCgCA  J   SEQ ID NO:31
GCCCACGGTGTCACCTCGGCCCCGGAgAgCAGGCCGGCCCtGGGCTCCACCGCCCCCCCA  K   SEQ ID NO:32
GCCCACGGTGTCACCTCGGCCCCGGACACCAGGCCGGCCCCGGGCTCCACCGCaCCCCCA  V   SEQ ID NO:33
GCCCACGGTGTCACCTCGGCCCCGGACACCAGGCCGGCCCCGGGCTCCACCGCCCCCCCg  W   SEQ ID NO:34

GCCCACGGTGTCACCTCGGCCCCGGACACCAGGCGGGCCCCGGGCTCCACCCCGGCCCCG  6   SEQ ID NO:35
GCCCACGGTGTCACCTCGGCCCCGGACACCAGGCcGGCCCCGGGCTCCACCCCGGCCCCG  6'  SEQ ID NO:36
GGCTCCACCGCCCCCCAGCCCACGGTGTCACCTCGGCCCCGGACACCAGGCCGGCCCCG   7   SEQ ID NO:37
GGCTCCACCGCCCCCCAGCCCATGGTGTCACCTCGGCCCCGGACAACAGGCCCGCCTTG   8   SEQ ID NO:38
GGCTCCACCGCCCCTCCAGTCCACAATGTCACCTCGGCCTCAGGCTCTGCATCAGGCTCA  9   SEQ ID NO:39
```

Figure 4

(a) CEPH mother (NA12892), short allele = CEPH child short allele 1-2-3-4-5-C-X-D-E-C-F-X-X-A-B-D-E-C-X-X-W-A-A-B-X-X-G-A-B-X-X-X-X-X-X-
V-6'-7-8-9

(b) CEPH mother (NA12892), long allele 1-2-3-4-5-C-X-D-E-C-X-H-X-A-B-D-E-C-X-X-X-A-A-B-X-X-X-X-X-X-X-X-X-I-X-
A-J-B-X-X-X-X-X-V-6'-7-8-9

(c) CEPH father (NA12891), short allele 1-2-3-4-5-C-X-D-E-C-F-X-X-A-B-D-E-C-X-X-X-A-A-B-X-X-X-X-X-G-A-B-X-X-X-
X-X-X-V-6'-7-8-9

(d) CEPH father (NA12891), long allele = CEPH child long allele 1-2-3-4-5-C-X-D-E-C-X-X-X-A-A-B-X-X-X-X-X-A-A-B-X-X-X-X-X-A-A-X-X-X-
X-X-X-X-X-A-A-B-X-X-X-X-B-B-X-X-A-A-B-X-X-X-B-A-A-X-X-X-X-X-X-X-V-6-7-
8-9

(e) F1:II-2 = F5:IV-5 = F6:IV-3= F6:IV-4 non-risk alleles 1-2-3-4-5-C-X-D-E-C-F-X-X-A-B-D-E-C-X-X-X-A-A-B-X-X-X-X-X-G-A-B-X-X-
X-X-X-X-V-6'-7-8-9

(f) F1:III-5

(a) F4:IV-2 (identical to F4:V-3 assembly)

1-2-3-4-5-C-X-D-E-C-F-X-X-A-B-D-E-C-X-X-X-A-A-B-X-X-X-X-X-X-G-A-B-X-X-
X-X-X-X-V-6'-7-8-9

(b) F6:IV-3

1-2-3-4'-5-C-X-D-X-A-A-A-A-B-X-X-X-X-B-A-A-B-X-X-X-X-X-X-G-A-B-X-X-X-
X-X-X-X-X-6-7-8-9

(c) F2:IV-3

1-2-3-4-5-C-X-D-E-C-X-H-X-A-A-B-D-E-C-X-X-X-A-A-B-X-X-X-X-X-E-C-X-X-X-
A-A-B-X-X-X-X-X-X-X-X-X-X-X-X-V-X-A-J-B-X-X-X-X-X-X-V-6'-7-8-9

SEQUENCE LISTING

<160> NUMBER OF SEQ ID NOS: 43

<210> SEQ ID NO 1
<211> LENGTH: 11
<212> TYPE: DNA
<213> ORGANISM: Homo sapiens

<400> SEQUENCE: 1
gcccccccag c                                                          11

<210> SEQ ID NO 2
<211> LENGTH: 12
<212> TYPE: DNA
<213> ORGANISM: Homo sapiens

<400> SEQUENCE: 2
gcccccccca gc                                                         12

<210> SEQ ID NO 3
<211> LENGTH: 19
<212> TYPE: DNA
<213> ORGANISM: Artificial Sequence
<220> FEATURE:

```
<223> OTHER INFORMATION: Chemically synthesized probe

<400> SEQUENCE: 3
cgggctccac cgcccccc                                                    19

<210> SEQ ID NO 4
<211> LENGTH: 37
<212> TYPE: DNA
<213> ORGANISM: Artificial Sequence
<220> FEATURE:
<223> OTHER INFORMATION: Chemically synthesized primer

<400> SEQUENCE: 4
ctgggaatcg caccagcgtg tggccccggg ctccacc                               37

<210> SEQ ID NO 5
<211> LENGTH: 39
<212> TYPE: DNA
<213> ORGANISM: Artificial Sequence
<220> FEATURE:
<223> OTHER INFORMATION: Chemically synthesized primer

<400> SEQUENCE: 5
cgtggatgag gagccgcagt gtccggggcc gaggtgaca                             39

<210> SEQ ID NO 6
<211> LENGTH: 20
<212> TYPE: DNA
<213> ORGANISM: Artificial Sequence
<220> FEATURE:
<223> OTHER INFORMATION: Mutant extension product

<400> SEQUENCE: 6
cgggctccac cgcccccccc                                                  20

<210> SEQ ID NO 7
<211> LENGTH: 21
<212> TYPE: DNA
<213> ORGANISM: Artificial Sequence
<220> FEATURE:
<223> OTHER INFORMATION: Wild-type extension product

<400> SEQUENCE: 7
cgggctccac cgccccccca g                                                21

<210> SEQ ID NO 8
<211> LENGTH: 98
<212> TYPE: DNA
<213> ORGANISM: Artificial Sequence
<220> FEATURE:
<223> OTHER INFORMATION: Chemically synthesized probe

<400> SEQUENCE: 8
cagcccacgg tgtcacctcg gccccggaca ccaggccggc cccgggccca ccgcccccc       60 agcccacggt gtcacccggc cccggacacc aggccggc                              98

<210> SEQ ID NO 9
<211> LENGTH: 27
<212> TYPE: DNA
<213> ORGANISM: Artificial Sequence
<220> FEATURE:
<223> OTHER INFORMATION: Chemically synthesized primer

<400> SEQUENCE: 9
ggagaaaagg agacttcggc tacccag                                          27
```

<210> SEQ ID NO 10
<211> LENGTH: 27
<212> TYPE: DNA
<213> ORGANISM: Artificial Sequence
<220> FEATURE:
<223> OTHER INFORMATION: Chemically synthesized primer

<400> SEQUENCE: 10
gccgttgtgc accagagtag aagctga                                27

<210> SEQ ID NO 11
<211> LENGTH: 23
<212> TYPE: DNA
<213> ORGANISM: Artificial Sequence
<220> FEATURE:
<223> OTHER INFORMATION: Chemically synthesized primer

<400> SEQUENCE: 11
gggtgcgcat gatcctctag agt                                    23

<210> SEQ ID NO 12
<211> LENGTH: 25
<212> TYPE: DNA
<213> ORGANISM: Artificial Sequence
<220> FEATURE:
<223> OTHER INFORMATION: Chemically synthesized primer

<400> SEQUENCE: 12
taaattgcac tgaaatctag aaata                                  25

<210> SEQ ID NO 13
<211> LENGTH: 37
<212> TYPE: DNA
<213> ORGANISM: Artificial Sequence
<220> FEATURE:
<223> OTHER INFORMATION: Chemically synthesized primer

<400> SEQUENCE: 13
ctgggaatcg caccagcgtg tggccccggg ctccacc                     37

<210> SEQ ID NO 14
<211> LENGTH: 39
<212> TYPE: DNA
<213> ORGANISM: Artificial Sequence
<220> FEATURE:
<223> OTHER INFORMATION: Chemically synthesized primer

<400> SEQUENCE: 14
cgtggatgag gagccgcagt gtccggggcc gaggtgaca                   39

<210> SEQ ID NO 15
<211> LENGTH: 60
<212> TYPE: DNA
<213> ORGANISM: Homo sapiens

<400> SEQUENCE: 15
aaggagactt cggctaccca gagaagttca gtgcccagct ctactgagaa gaatgctgtg    60

<210> SEQ ID NO 16
<211> LENGTH: 60
<212> TYPE: DNA
<213> ORGANISM: Homo sapiens

<400> SEQUENCE: 16
agtatgacca gcagcgtact ctccagccac agcccggtt caggctcctc caccactcag    60

<210> SEQ ID NO 17
<211> LENGTH: 60
<212> TYPE: DNA
<213> ORGANISM: Homo sapiens

<400> SEQUENCE: 17
ggacaggatg tcactctggc cccggccacg gaaccagctt caggttcagc tgccacctgg    60

<210> SEQ ID NO 18
<211> LENGTH: 60
<212> TYPE: DNA
<213> ORGANISM: Homo sapiens

<400> SEQUENCE: 18
ggacaggatg tcacctcggt cccagtcacc aggccagccc tgggctccac caccccgcca    60

<210> SEQ ID NO 19
<211> LENGTH: 60
<212> TYPE: DNA
<213> ORGANISM: Homo sapiens

<400> SEQUENCE: 19
ggacaggatg tcacctcggt cccagtcacc aggccagccc tgggctccac caccccacca    60

<210> SEQ ID NO 20
<211> LENGTH: 60
<212> TYPE: DNA
<213> ORGANISM: Homo sapiens

<400> SEQUENCE: 20
gcccacgatg tcacctcagc cccggacaac aagccagccc cgggctccac cgccccccca    60

<210> SEQ ID NO 21
<211> LENGTH: 60
<212> TYPE: DNA
<213> ORGANISM: Homo sapiens

<400> SEQUENCE: 21
gcccacggtg tcacctcggc cccggacacc aggccggccc cgggctccac cgccccccca    60

<210> SEQ ID NO 22
<211> LENGTH: 60
<212> TYPE: DNA
<213> ORGANISM: Homo sapiens

<400> SEQUENCE: 22
gcccacggtg tcacctcggc cccggagagc aggccggccc cgggctccac cgcgcccgca    60

<210> SEQ ID NO 23
<211> LENGTH: 60
<212> TYPE: DNA
<213> ORGANISM: Homo sapiens

<400> SEQUENCE: 23
gcccacggtg tcacctcggc cccggagagc aggccggccc cgggctccac cgccccccca    60

<210> SEQ ID NO 24
<211> LENGTH: 60
<212> TYPE: DNA
<213> ORGANISM: Homo sapiens

<400> SEQUENCE: 24

```
gcccacggtg tcacctcggc cccggacacc aggccggccc cgggctccac cgccccccaa     60
```

<210> SEQ ID NO 25
<211> LENGTH: 60
<212> TYPE: DNA
<213> ORGANISM: Homo sapiens

<400> SEQUENCE: 25

```
gcccacggtg tcacctcggc cccggacacc aggcccgccc cgggctccac cgccccccca     60
```

<210> SEQ ID NO 26
<211> LENGTH: 60
<212> TYPE: DNA
<213> ORGANISM: Homo sapiens

<400> SEQUENCE: 26

```
gcccacggtg tcacctcggc cccggacacc aggcccgccc cgggctccac cgcgcccgca     60
```

<210> SEQ ID NO 27
<211> LENGTH: 60
<212> TYPE: DNA
<213> ORGANISM: Homo sapiens

<400> SEQUENCE: 27

```
gcccacggtg tcacctcggc cccggacacc aggccggccc cgggctccac cgcccccaca     60
```

<210> SEQ ID NO 28
<211> LENGTH: 60
<212> TYPE: DNA
<213> ORGANISM: Homo sapiens

<400> SEQUENCE: 28

```
gcccacggtg tcacctcggc cccggacacc aggccggccc cgggctccac cgcgcccgca     60
```

<210> SEQ ID NO 29
<211> LENGTH: 60
<212> TYPE: DNA
<213> ORGANISM: Homo sapiens

<400> SEQUENCE: 29

```
gcccacggtg tcacctcggc cccggacacc aggccggccc cgggctccac cgccgcccca     60
```

<210> SEQ ID NO 30
<211> LENGTH: 60
<212> TYPE: DNA
<213> ORGANISM: Homo sapiens

<400> SEQUENCE: 30

```
gcccacggtg tcacctcggc cccggacacc aggccggccc cgggctccac cgcgccccca     60
```

<210> SEQ ID NO 31
<211> LENGTH: 60
<212> TYPE: DNA
<213> ORGANISM: Homo sapiens

<400> SEQUENCE: 31

```
gcccacggtg tcacctcggc accggagagc aggccggccc cgggctccac cgcgcccgca     60
```

<210> SEQ ID NO 32
<211> LENGTH: 60
<212> TYPE: DNA
<213> ORGANISM: Homo sapiens

<400> SEQUENCE: 32
gcccacggtg tcacctcggc cccggagagc aggccggccc tgggctccac cgcccccca        60

<210> SEQ ID NO 33
<211> LENGTH: 60
<212> TYPE: DNA
<213> ORGANISM: Homo sapiens

<400> SEQUENCE: 33
gcccacggtg tcacctcggc cccggacacc aggccggccc cgggctccac cgcaccccca        60

<210> SEQ ID NO 34
<211> LENGTH: 60
<212> TYPE: DNA
<213> ORGANISM: Homo sapiens

<400> SEQUENCE: 34
gcccacggtg tcacctcggc cccggacacc aggccggccc cgggctccac cgccccccg        60

<210> SEQ ID NO 35
<211> LENGTH: 60
<212> TYPE: DNA
<213> ORGANISM: Homo sapiens

<400> SEQUENCE: 35
gcccacggtg tcacctcggc cccggacacc aggcgggccc cgggctccac cccggccccg        60

<210> SEQ ID NO 36
<211> LENGTH: 60
<212> TYPE: DNA
<213> ORGANISM: Homo sapiens

<400> SEQUENCE: 36
gcccacggtg tcacctcggc cccggacacc aggccggccc cgggctccac cccggccccg        60

<210> SEQ ID NO 37
<211> LENGTH: 60
<212> TYPE: DNA
<213> ORGANISM: Homo sapiens

<400> SEQUENCE: 37
ggctccaccg cccccccagc ccacggtgtc acctcggccc cggacaccag gccggccccg        60

<210> SEQ ID NO 38
<211> LENGTH: 60
<212> TYPE: DNA
<213> ORGANISM: Homo sapiens

<400> SEQUENCE: 38
ggctccaccg cccccccagc ccatggtgtc acctcggccc cggacaacag gcccgccttg        60

<210> SEQ ID NO 39
<211> LENGTH: 60
<212> TYPE: DNA
<213> ORGANISM: Homo sapiens

<400> SEQUENCE: 39
ggctccaccg cccctccagt ccacaatgtc acctcggcct caggctctgc atcaggctca        60

<210> SEQ ID NO 40
<211> LENGTH: 21
<212> TYPE: DNA
<213> ORGANISM: Homo sapiens

```
<400> SEQUENCE: 40 accgccccc cagcccacgg t                                                  21

<210> SEQ ID NO 41
<211> LENGTH: 7
<212> TYPE: PRT
<213> ORGANISM: Homo sapiens

<400> SEQUENCE: 41

Thr Ala Pro Pro Ala His Gly
1               5

<210> SEQ ID NO 42
<211> LENGTH: 22
<212> TYPE: DNA
<213> ORGANISM: Homo sapiens

<400> SEQUENCE: 42 accgccccc ccagcccacg gt                                                 22

<210> SEQ ID NO 43
<211> LENGTH: 7
<212> TYPE: PRT
<213> ORGANISM: Homo sapiens

<400> SEQUENCE: 43

Thr Ala Pro Pro Ser Pro Arg
1               5
```

METHODS OF DIAGNOSING AND TREATING MEDULLARY CYSTIC KIDNEY DISEASE

RELATED APPLICATIONS AND INCORPORATION BY REFERENCE

This application is a continuation-in-part application of international patent application Serial No. PCT/US2013/054301 filed Aug. 9, 2013, which published as PCT Publication No. WO 2014/026092 on Feb. 13, 2014, which claims benefit of and priority to U.S. Provisional Application No. 61/681,937, filed on Aug. 10, 2012.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. More specifically, all referenced documents are incorporated by reference to the same extent as if each individual document was specifically and individually indicated to be incorporated by reference.

FIELD OF THE INVENTION

This invention relates to the identification of a frameshift mutation in the VNTR region of the MUC1 gene in subject having medullary cystic kidney disease and an assay to identify subjects having this mutation that is useful in the diagnosis of the disease.

SEQUENCE LISTING

The instant application contains a Sequence Listing which has been submitted electronically in ASCII format and is hereby incorporated by reference in its entirety. Said ASCII copy is named 46783012094.txt and is 8 kb in size.

BACKGROUND OF THE INVENTION

Medullary cystic kidney disease (MCKD) type 1 is a rare disorder characterized by autosomal dominant inheritance of tubulo-interstitial kidney disease (Bleyer et al., 2010, *Semin. Nephrol* 30, 366-373). Affected individuals develop a slow deterioration in kidney function (specifically, in glomerular filtration rate), usually commencing in the second to third decade of life and resulting in the need for dialysis or kidney transplantation approximately two decades later. Diagnosis of MCKD1 in patients is complicated by the disease's variable severity and age at onset, its absence of extrarenal manifestations, and its absence of characteristic renal manifestations such as hematuria, proteinuria, nephrolithiasis, or pathognomonic morphological changes in the kidney. These characteristics, together with the high frequency of kidney disease in the general population (Castro et al., 2009, *Am. J. Kidney Dis.* 53, S46-S55), have complicated individual diagnosis and have hampered MCKD1 research. Diagnostic difficulties have also prevented living related kidney donation, as potential donor family members have not known their status as unaffected or (yet-to-be) affected. Conclusive determination of the molecular bases of MCKD1 would lead both to much-needed diagnostics for families and to general functional insights into the pathogenesis of tubulo-interstitial kidney disease, which could inform prevention and therapy.

Despite these potential challenges, MCKD1 has been compellingly and consistently mapped to a single autosomal locus at 1q21. First linked in a large Cypriot population in 1998 (Christodoulou, K. et al., 1998, *Hum. Mol. Genet.* 119, 649-658), linkage to 1q21 has also been reported in several families from Finland (Auranen et al., 2001, *Kidney Int.* 60, 1225-1232), Saudia Arabia (Al-Romaih, K. I., et al., 2011, *Am. J. Kidney Dis.* 58, 186-195), a Native-American kindred (Kiser, R. L. et al, 2004, *Am. J. Kidney Dis.*, 44, 611-617), many additional families of European descent (Wolf, M. T. F. et al, 2006, *Hum. Genet.* 7, 905-911; Fuchshuber, A. et al., 2001, *Genomics,* 72, 278-284), and a family with co-existing bipolar disease. Attempts to identify the mutated gene(s), however, have not been successful; mutational analysis of 37 candidate genes within the linked interval in 23 MCKD1 patients was unable to identify the causative genetic mutation(s) (Wolf, M. T. F. et al, 2006, *Hum. Genet.* 7, 905-911).

The advent of massively parallel sequencing (MPS) technologies has made exhaustive sequencing of genomic regions a viable approach to the identification of genes responsible for rare Mendelian diseases caused by high penetrance mutations. Yet, there is also a growing recognition that using MPS to discover disease genes is not always straightforward.

Citation or identification of any document in this application is not an admission that such document is available as prior art to the present invention.

SUMMARY OF THE INVENTION

This invention based upon the discovery of a frameshift mutation in the GC-rich variable number of tandem repeats (VNTR) sequence of the coding region of the mucin 1 gene (MUC-1). This frameshift mutation results an insertion of an extra cytosine (C) within a run of seven Cs in one copy of the repeat. The mutation gives rise to a novel peptide repeat before premature termination.

The present invention features a method of diagnosing or determining a predisposition to developing medullary cystic kidney disease type 1 (MCKD1) which may comprise detecting a point mutation resulting in insertion of a cytosine in the GC-rich variable number of tandem repeats (VNTR) sequence of the coding region of the mucin 1 gene (MUC-1), wherein the presence of the point mutation indicates that the subject has or is predisposed to developing MCKD1.

The present invention features a method of diagnosing a frameshift mutation in a subject which may comprise analyzing a sample to determine the presence or absence of a frameshift mutation in the GC-rich variable number of tandem repeats (VNTR) sequence, wherein said frameshift mutation produces a mutant 8G homopolymer. In one aspect, the frameshift mutation produces a truncated MUC-1 polypeptide having a pI (isoelectric point) greater that the wildtype MUC-1 polypeptide. In one aspect, the sample is a nucleic acid sample. In another aspect, the nucleic acid is DNA, RNA or cDNA. In another aspect, the sample is any sample containing the truncated MUC-1 polypeptide.

The present invention features an assay for determining a cytosine insertion in the GC-rich variable number of tandem repeats (VNTR) sequence of the coding region of the mucin 1 gene (MUC-1) which may comprise: a) performing an endonuclease digestion on a nucleic acid sample, wherein said endonuclease selectively cleaves a wild-type MUC-1 nucleic acid sequence and not a mutant MUC-1 sequence having a cytosine insertion in the GC-rich variable number of tandem repeats (VNTR) region to produce a first plurality of nucleic acid fragments, b) performing a PCR reaction on said first plurality of nucleic acid fragments to produced a plurality of amplified nucleic acid products, performing a second endonuclease digestion on the plurality of amplified nucleic acid products, wherein the endonuclease selectively cleaves a wild-type MUC-1 nucleic acid sequence and not a mutant MUC-1 sequence having a cytosine insertion in the GC-rich variable number of tandem repeats (VNTR) region to produce a second plurality of nucleic acid fragments, c) performing a probe extension reaction on the second plurality of nucleic acid fragments using a probe that specifically binds upstream of the cytosine insertion to produce a plurality of reaction products, and d) detecting the presence of a reaction product containing the cytosine insertion, thereby determining a cytosine insertion in the GC-rich variable number of tandem repeats (VNTR) sequence of the coding region of the mucin 1 gene (MUC-1). In one aspect, the invention features an assay wherein the endonuclease specifically cleaves a nucleic acid having the nucleic acid sequence GCCCCCCCAGC (SEQ ID NO: 1) and not a mutant sequence having the nucleic acid sequence GCCCCCCCCAGC (SEQ ID NO: 2). In one aspect, the invention features an assay wherein the endonuclease is MwoI. In one aspect, the invention features an assay wherein the probe may comprise the nucleic acid sequence CGGGCTCCACCGCCCCCCC (SEQ ID NO: 3). In one aspect, the invention features an assay wherein the detecting is performed by size exclusion chromatography. In one aspect, the invention features an assay wherein the detecting is performed by mass spectroscopy. In one aspect, the invention features an assay wherein the reaction product containing the cytosine insertion is about 5,904 daltons. In one aspect, the invention features an assay wherein a purification step is performed before step (b), (c) and or (d). In one aspect, the invention features an assay wherein the nucleic acid sample is DNA, RNA or cDNA.

The present invention provides a method of treating or alleviating a symptom of MCKD1 which may comprise, administering to a subject a compound that inhibits the expression for activity of MUC-1. In one aspect, the compound is an antisense MUC-1 nucleic acid, a MUC-1 specific short-interfering RNA, or a MUC-1 specific ribozyme. In one aspect, the sample is a nucleic acid sample.

In any of the foregoing methods, the sample is a nucleic acid sample.

In any of the foregoing methods, the nucleic acid is DNA, RNA or cDNA.

In any of the foregoing methods, the sample is any sample containing the truncated MUC-1 polypeptide.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description and claims.

Accordingly, it is an object of the invention not to encompass within the invention any previously known product, process of making the product, or method of using the product such that Applicants reserve the right and hereby disclose a disclaimer of any previously known product, process, or method. It is further noted that the invention does not intend to encompass within the scope of the invention any product, process, or making of the product or method of using the product, which does not meet the written description and enablement requirements of the USPTO (35 U.S.C. § 112, first paragraph) or the EPO (Article 83 of the EPC), such that Applicants reserve the right and hereby disclose a disclaimer of any previously described product, process of making the product, or method of using the product. It may be advantageous in the practice of the invention to be in compliance with Art. 53(c) EPC and Rule 28(b) and (c) EPC. Nothing herein is to be construed as a promise.

It is noted that in this disclosure and particularly in the claims and/or paragraphs, terms such as "comprises", "comprised", "comprising" and the like can have the meaning attributed to it in U.S. patent law; e.g., they can mean "includes", "included", "including", and the like; and that terms such as "consisting essentially of" and "consists essentially of" have the meaning ascribed to them in U.S. patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

FIG. 1. Common 60-mer units found within and near the MUC1 VNTR. Oriented relative to the coding strand of MUC1 (negative strand of hg19), 60-mer units 1-5 (including variant 4') appear near the beginning of the VNTR, whereas 6-9 (and variant 6') appear near the end. The rest are in the middle, and are very similar to the 'canonical' unit X, with variant bases shown in lower case. The underlined base in structure 9 corresponds to hg19 chr1 position 155,160, 963, and the underlined base in structure 1 corresponds to hg19 chr1 position 155,162,030.

FIG. 4. Complete assemblies of non-risk alleles. In several instances, the structure of the non-risk MUC1-VNTR allele was determined exactly. Each assembly is depicted as a series of 60-mer units (see FIG. 1) covering hg19 chr1 positions 155,160,963 to 155,162,030 (inclusive), and oriented relative to the MUC1 coding strand (hg 19 negative strand).

FIG. 5. Complete assemblies of risk alleles from three families. For families 2, 4, and 6 the structure of the risk MUC1-VNTR allele was determined almost exactly, and Applicants are thus able to determine the position of the mutant repeat unit and its sequence context, both of which are different in all three cases. Each assembly is depicted as a series of 60-mer units (see FIG. 1) covering hg19 chr1 positions 155,160,963 to 155,162,030 (inclusive), and oriented relative to the MUC1 coding strand (hg 19 negative strand). Units shown in red contain the insertion of an extra C into the $C^7$ sequence appearing at positions 53-59. For (a) and (b), the exact allele structure is shown, whereas for (c), the structure is completely determined except for the exact length of the stretch X-X-X-X-X-X-X-X-X-X-X-X-X-X (14 copies, shown in blue), whose predicted length from the gel size is 13.8 copies, and which, given limitations in gel measurement accuracy, could in fact be 13, 14 or 15 copies.

DETAILED DESCRIPTION OF THE INVENTION

Figure 2:
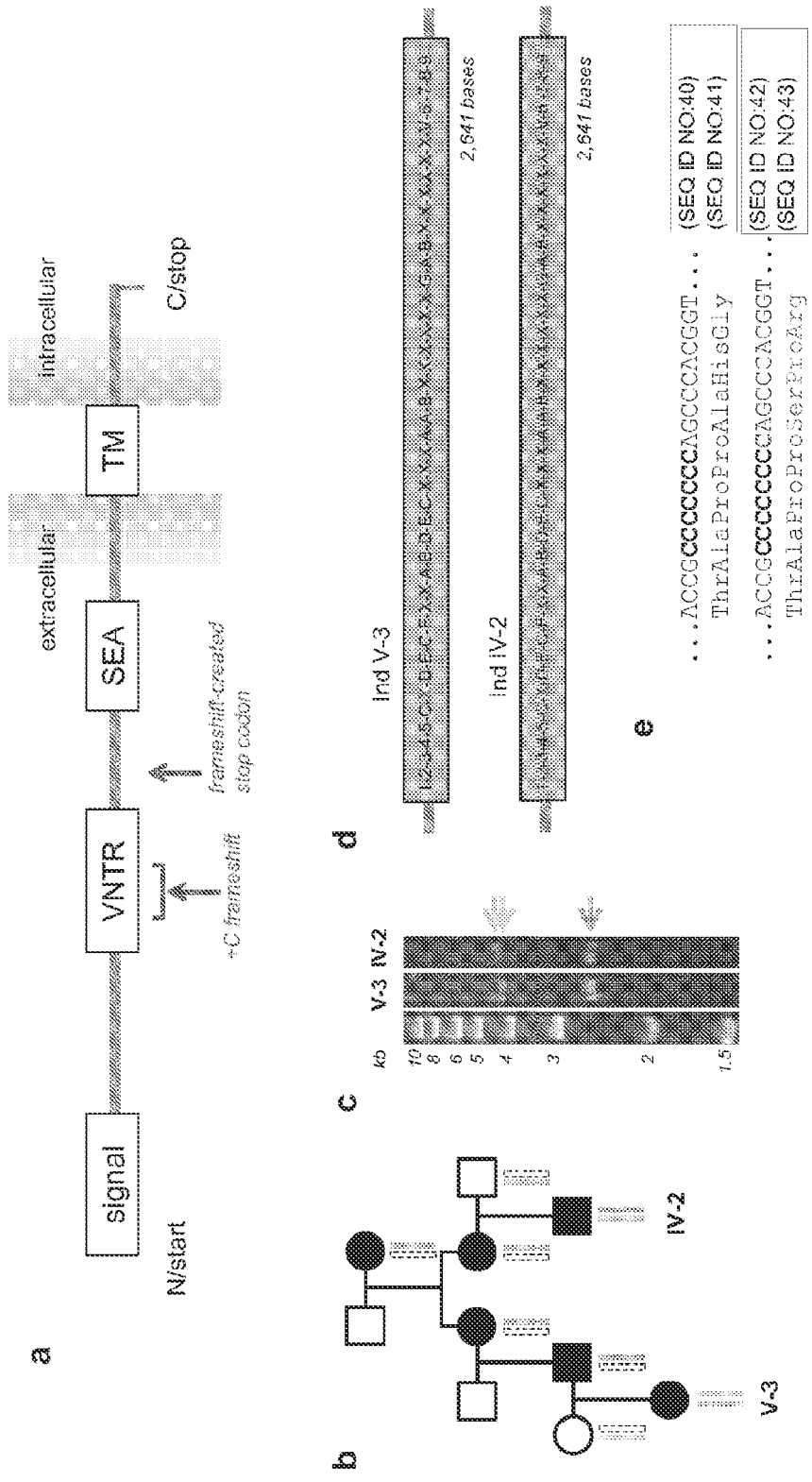
FIG. 2. Discovery of +C insertion within MUC1 coding VNTR. (a) The major domains of the full-length MUC1 protein are shown: N-terminal signal sequence, VNTR, SEA module (where cleavage occurs), transmembrane domain, and C-terminal cytoplasmic domain. Based on fully and unambiguously assembled VNTR alleles, the frameshift caused by insertion of a C in the coding strand (as described in the main text) is expected to introduce a novel stop codon shortly beyond the VNTR domain. (b and c) Where possible, knowledge of segregating phased SNP-marker haplotypes was used to select for de novo VNTR sequencing and assembly those individuals sharing only a single haplotype across the region, as this aided identification of the VNTR allele segregating with the shared risk haplotype. (d and e) Independent de novo assembly of the shared VNTR allele in two individuals from family 4 shows exactly identical complete sequence, with the seventh 60-base unit (red X) out of 44 containing a +C insertion event. The assembly is oriented relative to the coding strand of MUG1 and covers bases chr1:155,160,963-155,162,030 (hg19). Each unique 60-base repeat segment is represented by a different letter or number (see FIG. 1). (e) Translational impact of +C frameshift.

This invention based upon the discovery of a frameshift mutation in the GC-rich variable number of tandem repeats (VNTR) sequence of the coding region of the mucin 1 gene (MUC-1). This frameshift mutation results an insertion of an extra cytosine (C) within a run of seven Cs in one copy of the repeat. The mutation gives rise to a novel peptide repeat before premature termination. A MUC-1 containing the frameshift mutation is also referred to herein as MUC1-fs.

This mutation was identified using a combination of classical and modern approaches to positional cloning. The effort required underscores why current MPS technology may not suffice to reveal disease mutations, even in a case where linkage analysis pinpoints the implicated gene to a region of a few megabases.

The MCKD1 mutations predict a truncated MUC1 polypeptide having significant amounts of novel sequence generated by frameshifting. Immunospecific detection confirmed the presence of the predicted mutant gene product in renal tubular epithelial cells, demonstrating biosynthesis, accumulation, and partial mislocalization of the mutant MUC1-fs protein. Notably, the novel repeat sequence caused by the frameshift has a very different charge (pI=12.2) than the wild-type repeat sequence (pI=7.3). The term "pI" refers to isoelectric point, or the pH at which the particular molecule (i.e., nucleic acid) carries no net electrical charge.

This invention provides a robust and reliable assay for detecting a single base insertion/frame shift mutation located within the VNTR region of the MUC1 gene. This frame shift mutation, thought to be an autosomal dominant variation, appears to be strongly associated with MCKD1.

Accordingly, in one aspect the invention provides a method of diagnosing or determining a predisposition to developing MCKD1 by detecting an insertion of a cytosine in the VNTR region of the MUC1 gene.

The high GC content (~82%) of the region, together with the variable insertion position within the VNTR region and the shear number of wildtype repeat sequences (anywhere from 40-80 tandem repeats of the 60-mer sequence) would swamp the signal for any direct detection of the mutation using standard commercial genotyping methods, thereby increasing the difficulty in differentiating between mutant signal and background wild-type signal. Accordingly, in another aspect the invention provides an assay for detecting the frameshift mutation. In particular, the assay method described herein, unlike direct next generation sequencing, has the ability to enrich for the mutant signal over background as well as tolerate the high GC content of this tandem repeat region.

The key concept on which the assay is based is the enrichment for the mutant signal over wildtype background using a restriction endonuclease which specifically targets and digests the 7G homopolymer sequence. Iterative rounds of locus specific PCR amplification and restriction digestion is followed by probe extension and mass detection by MALDI-TOF mass spectrometry. This allows for the clear detection of the single base insertion event.

The identified mutations and the genotyping assay described herein provide a potential screening tool for younger members of families in which MCKD1 has been previously diagnosed, as well as in potential sporadic cases. Additionally, knock-out studies indicate that the MUC1 gene is not essential in mice. Together with the dominant and late-onset nature of the disease, this raises the possibility of preventative or therapeutic approaches based on treatments that decrease expression of the MUC1 gene or splice out its single VNTR-encoding exon.

Diagnostic and Therapeutic Methods

The invention provides methods of diagnosing a frameshift mutation in a subject by analyzing a DNA sample to determine the presence or absence of a frameshift mutation in the GC-rich variable number of tandem repeats (VNTR) sequence. The frameshift mutation results in the insertion of a cytosine in the GC-rich variable number of tandem repeats (VNTR) sequence of the coding region of the mucin 1 gene (MUC-1). The frameshift mutation produces a mutant 8G homopolymer. The mutation predicts a truncated MUC1 polypeptide having significant amounts of novel sequence generated by frameshifting. Immunospecific detection confirmed the presence of the predicted mutant gene product in renal tubular epithelial cells, demonstrating biosynthesis, accumulation, and partial mislocalization of the mutant MUC1-fs protein. The novel repeat sequence caused by the frameshift has a pI greater that the wildtype MUC-1 polypeptide. Identification of the frameshift indicates the subject has or is predisposed to developing medullary cystic kidney disease type 1 (MCKD1).

The frameshift mutation can be detected by any method know in the art or preferably by the assay method described herein.

In one aspect, the method for diagnosing or determining a predisposition to developing medullary cystic kidney disease type 1 (MCKD1) or diagnosing a frameshift may include the following steps: a) performing an endonuclease digestion on a nucleic acid sample, wherein said endonuclease selectively cleaves a wild-type MUC-1 nucleic acid sequence and not a mutant MUC-1 sequence having a cytosine insertion in the GC-rich variable number of tandem repeats (VNTR) region to produce a first plurality of nucleic acid fragments, b) performing a PCR reaction on said first plurality of nucleic acid fragments to produced a plurality of amplified nucleic acid products, performing a second endonuclease digestion on the plurality of amplified nucleic acid products, wherein the endonuclease selectively cleaves a wild-type MUC-1 nucleic acid sequence and not a mutant MUC-1 sequence having a cytosine insertion in the GC-rich variable number of tandem repeats (VNTR) region to produce a second plurality of nucleic acid fragments, c) performing a probe extension reaction on the second plurality of nucleic acid fragments using a probe that specifically binds upstream of the cytosine insertion to produce a plurality of reaction products, and d) detecting the presence of a reaction product containing the cytosine insertion, thereby determining a cytosine insertion in the GC-rich variable number of tandem repeats (VNTR) sequence of the coding region of the mucin 1 gene (MUC-1). In one aspect, the invention features a method for determining a cytosine insertion in the GC-rich variable number of tandem repeats (VNTR) sequence of the coding region of the mucin 1 gene (MUC-1).

The sample can be any biological sample such as a tissue or fluid. Various embodiments include cells of the skin, muscle, fascia, brain, prostate, breast, endometrium, lung, head & neck, pancreas, small intestine, blood cells, liver, testes, ovaries, colon, rectum, skin, stomach, esophagus, spleen, lymph nodes, bone marrow or kidney. Other embodiments include fluid samples such as peripheral blood, lymph fluid, ascites, serous fluid, pleural effusion, sputum, cerebrospinal fluid, lacrimal fluid, stool urine or amniotic fluid. Nucleic acids used are isolated from cells contained in the biological sample, according to standard methodologies (Sambrook et al., 1989).

The nucleic acids may be DNA (e.g., genomic DNA, mitochondrial DNA), or RNA (e.g., mRNA, structural RNA), or cDNA (e.g., reverse-transcribed using methods known in the art from RNA).

The invention provides a method for detecting one or more sequence changes in a plurality of target nucleic acid sequences in a nucleic acid sample which may comprise five steps. The five steps are described in more detail below.

Step (a) Endonuclease Digestion of a Nucleic Acid Sample

In the first step, endonuclease digestion is performed on a nucleic acid sample, for example, DNA, to produce a first plurality of DNA fragments. The endonuclease is chosen to specifically target and digest the wild-type 7G homopolymer sequence (GCCCCCCCAGC (SEQ ID NO:1)) compared to the mutant 8G homopolymer sequence (GCCCCCCCCAGC (SEQ ID NO:2)). The endonuclease is for example MwoI. For example, the 100 ng of nucleic acid sample (e.g., DNA) is digested with 5 U of MwoI for 16 hours at 60° C. Optimal reaction and digestion conditions for performing the endonuclease digestion are further described herein.

Step (b) PCR Amplification

In the second step, PCR amplification is performed on the first plurality of DNA fragments obtained from the first step, to enrich for the mutant insertion-containing fragments over wild-type background. The plurality of DNA fragments are amplified using, for example, tailed primers nested within the 60-bp VNTR repeat. The primers specifically amplify intact VNTR fragments and produce a plurality of amplified DNA fragments. Examples of such primers are: InterMuc_L (CTGGGAATCGCACCAGCGTGTGGCCCCGGGCTC-CACC (SEQ ID NO:4)) InterMuc_R (CGTGGATGAG-GAGCCGCAGTGTCCGGGGCCGAGGTGACA (SEQ ID NO:5)). For example, the PCR reaction is performed using 18.5 ul of the digestion reaction, 5 U of HotStart Plus Taq, and 10 uM of primers in each reaction. For example, the PCR program features the denaturing step at 94° C. for 30 seconds, the annealing step at 67° C. for 30 seconds, and the elongation step at 72° C. for 1 minute for 45 cycles, and a final elongation step at 72° C. for 10 minutes. Additional reaction and amplification conditions for performing the PCR reaction are further described herein.

Step (c) Second Endonuclease Digestion

In the third step, endonuclease digestion is performed on the plurality of amplified DNA fragments in the second step (step (b)). As in the first step (step (a)), the endonuclease is chosen to specifically target and digest the wild-type 7G homopolymer sequence (GCCCCCCCAGC (SEQ ID NO:1)) compared to the mutant 8G homopolymer sequence (GCCCCCCCCAGC (SEQ ID NO:2)). The endonuclease is for example MwoI. For example, the 21.5 ul of the PCR product is digested with 5 U of MwoI for 16 or more hours at 60° C. Optimal reaction and digestion conditions for performing the endonuclease digestion are further described herein.

Step (d) Probe Extension

In the fourth step (step (d)), a probe extension reaction is performed using the second plurality of DNA fragments obtained from the third step (step (c)). The probe is designed to specifically bind upstream of the cytosine insertion. The probe extension is performed using a high fidelity DNA polymerase and a nucleotide termination mix containing dATP, ddCTP and ddGTP. The probe extension reaction produces a plurality of reaction products. For example, the probe is a 19 bp probe having the sequence of CGGGCTC-CACCGCCCCCCC (SEQ ID NO:3). For example, the probe extension reaction is performed with template from the second endonuclease digestion, 10 mM of nucleotide termination mix, a probe (e.g., SEQ ID NO:3), and 0.64 U of ThermoSequenase. For example, the probe extension reaction program features the denaturing step at 94° C. for 5 seconds, the annealing step at 52° C. for 5 seconds, and the elongation step at 72° C. for 5 seconds for a total of 55 cycles, and a final elongation step at 72° C. for 7 minutes.

Step (e) Detection of the Mutant 8G Homopolymer Sequence

In the fifth step (step (e)), the presence of the mutant 8G homopolymer sequence is detected. The mutant 8G homopolymer sequence is detected by any method known in the art. As the wildtype and mutant homopolymer are of different size, size exclusion chromatography is particular suited for detection of the mutant 8G homopolymer sequence. For example the mutant 8G homopolymer sequence is detected using mass spectroscopy such as MALDI-TOF mass-spectrometry using the Sequenom MassArray platform. Spectra are assessed for the presence of peaks corresponding to the mutant extension-product (CGGGCTCCACCGCCCCCCCC (SEQ ID NO:6)) at 5,904.83 daltons) and the wild-type extension-product (CGGGCTCCACCGCCCCCCCAG (SEQ ID NO:7)) at 6258.06 daltons).

Optionally prior to steps (b), (c) and/or (d) a purification step is performed by any method know in the art.

In another aspect, the invention provides methods of treating, alleviating a symptom or delaying the onset of MCKD1 by administering to a subject a compound that decreases the expression or activity of MUC-1.

A decrease in MUC-1 expression or activity can be defined by a reduction of a biological function of the MUC-1 protein. A MUC-1 biological function includes for example, such as lubrication and hydration of cell surfaces as well as protection from microorganisms and degradative enzymes. MUC-1 expression is measured by detecting a MUC-1 RNA transcript or protein. MUC-1 inhibitors are known in the art or are identified using methods described herein.

The MUC-1 inhibitor is for example an antisense MUC-1 nucleic acid, a MUC-1 specific short-interfering RNA, or a MUC-1 specific ribozyme.

By the term "siRNA" is meant a double stranded RNA molecule which prevents translation of a target mRNA. Standard techniques of introducing siRNA into a cell are used, including those in which DNA is a template from which an siRNA RNA is transcribed. The siRNA includes a sense MUC-1 nucleic acid sequence, an anti-sense MUC-1 nucleic acid sequence or both. Optionally, the siRNA is constructed such that a single transcript has both the sense and complementary antisense sequences from the target gene, e.g., a hairpin.

Binding of the siRNA to a MUC-1 transcript in the target cell results in a reduction in MUC-1 production by the cell. The length of the oligonucleotide is at least 10 nucleotides and may be as long as the naturally-occurring MUC-1 transcript. Preferably, the oligonucleotide is 19-25 nucleotides in length. Most preferably, the oligonucleotide is less than 75, 50, or 25 nucleotides in length.

The present invention provides for both prophylactic and therapeutic methods of treating a subject at risk of (or susceptible to) a disorder or having a disorder associated with aberrant (e.g., insufficient) metabolism. As used herein, the term "treatment" is defined as the application or administration of a therapeutic agent to a patient, or application or administration of a therapeutic agent to an isolated tissue or cell line from a patient, who has a disease, a symptom of disease or a predisposition toward a disease, with the purpose to cure, heal, alleviate, relieve, alter, remedy, ameliorate, improve or affect the disease, the symptoms of disease or the predisposition toward disease.

The compounds, e.g., MUC-1 inhibitors (also referred to herein as "active compounds") of the invention, and derivatives, fragments, analogs and homologs thereof, can be incorporated into pharmaceutical compositions suitable for administration. Examples of MUC-1 inhibitors include, but are not limited to, Go-201 and Go-203. Other MUC-1 inhibitors and methods of identifying such compounds are identified in US Publication No. 2011/0251246. Such compounds include a flavone having the structure

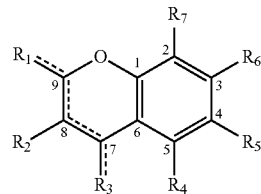

or a salt thereof, wherein $R_1$ is H, —OH, =O, substituted or unsubstituted alkyl($C_{1-8}$), alkoxy($C_{1-8}$), haloalkyl($C_{1-8}$), substituted phenyl or unsubstituted phenyl, wherein if $R_1$ is =O, $C_7$-$C_8$ is a double bond;

$R_2$ is H, —OH, alkyl($C_{1-8}$), substituted phenyl, unsubstituted phenyl, phenyl, phenyl thiazole, imidazole, pyrazole or furan;

$R_3$ is H, —OH, =O, halogen, haloalkyl($C_{1-8}$), substituted or unsubstituted alkyl($C_{1-8}$), substituted phenyl or unsubstituted phenyl, wherein if $R_3$ is =O, $C_8$-$C_9$ is a double bond;

$R_4$ is H or —OH;

$R_5$ is H, —OH, substituted or unsubstituted alkyl($C_{1-8}$) or alkoxy($C_{1-8}$), or $OR_8$, wherein $R_8$ is alkyl($C_{1-8}$), an ester or an amide;

$R_6$ is H, —OH, substituted or unsubstituted alkyl($C_{1-8}$) or alkoxy($C_{1-8}$), or $OR_8$, wherein $R_8$ is alkyl($C_{1-8}$), an ester or an amide; and $R_7$ is H, —OH, or substituted or unsubstituted alkyl($C_{1-8}$), with the proviso that $R_1$ and $R_3$ cannot both be =O.

The flavone may be Morin, Apigenin, Kaempferol, Fisetin, PD98059, 7-(benzyloxy)-4-(trifluoromethyl)-2H-chromen-2-one or 7-[(3-oxobutan-2-yl)oxy]-4-phenyl-2H-chromen-2-one, or a salt of any of the foregoing. Such compositions typically may comprise the peptide or mimetic, and a pharmaceutically acceptable carrier. As used herein, "pharmaceutically acceptable carrier" is intended to include any and all solvents, dispersion media, coatings, antibacterial and antifungal agents, isotonic and absorption delaying agents, and the like, compatible with pharmaceutical administration. Suitable carriers are described in the most recent edition of Remington's Pharmaceutical Sciences, a standard reference text in the field, which is incorporated herein by reference. Preferred examples of such carriers or diluents include, but are not limited to, water, saline, finger's solutions, dextrose solution, and 5% human serum albumin. Liposomes and non-aqueous vehicles such as fixed oils may also be used. The use of such media and agents for pharmaceutically active substances is well known in the art. Except insofar as any conventional media or agent is incompatible with the active compound, use thereof in the compositions is contemplated. Supplementary active compounds can also be incorporated into the compositions.

A pharmaceutical composition of the invention is formulated to be compatible with its intended route of administration. Examples of routes of administration include parenteral, e.g., intravenous, intradermal, subcutaneous, oral (e.g., inhalation), transdermal (topical), transmucosal, and rectal administration. Solutions or suspensions used for parenteral, intradermal, or subcutaneous application can include the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfate; chelating agents such as ethylenediaminetetraacetic acid; buffers such as acetates, citrates or phosphates, and agents for the adjustment of tonicity such as sodium chloride or dextrose. The pH can be adjusted with acids or bases, such as hydrochloric acid or sodium hydroxide. The parenteral preparation can be enclosed in ampoules, disposable syringes or multiple dose vials made of glass or plastic.

Pharmaceutical compositions suitable for injectable use include sterile aqueous solutions (where water soluble) or dispersions and sterile powders for the extemporaneous preparation of sterile injectable solutions or dispersion. For intravenous administration, suitable carriers include physiological saline, bacteriostatic water, Cremophor EL™ (BASF, Parsippany, N.J.) or phosphate buffered saline (PBS). In all cases, the composition must be sterile and should be fluid to the extent that easy syringeability exists. It must be stable under the conditions of manufacture and storage and must be preserved against the contaminating action of microorganisms such as bacteria and fungi. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. Prevention of the action of microorganisms can be achieved by various antibacterial and antifungal agents, for example, parabens, chlorobutanol, phenol, ascorbic acid, thimerosal, and the like. In many cases, it will be preferable to include isotonic agents, for example, sugars, polyalcohols such as manitol, sorbitol, sodium chloride in the composition. Prolonged absorption of the injectable compositions can be brought about by including in the composition an agent which delays absorption, for example, aluminum monostearate and gelatin.

Sterile injectable solutions can be prepared by incorporating the active compound (e.g., a MUC-1 inhibitor) in the required amount in an appropriate solvent with one or a combination of ingredients enumerated above, as required, followed by filtered sterilization. Generally, dispersions are prepared by incorporating the active compound into a sterile vehicle that contains a basic dispersion medium and the required other ingredients from those enumerated above. In the case of sterile powders for the preparation of sterile injectable solutions, methods of preparation are vacuum drying and freeze-drying that yields a powder of the active ingredient plus any additional desired ingredient from a previously sterile-filtered solution thereof.

Oral compositions generally include an inert diluent or an edible carrier. They can be enclosed in gelatin capsules or compressed into tablets. For the purpose of oral therapeutic administration, the active compound can be incorporated with excipients and used in the form of tablets, troches, or capsules. Oral compositions can also be prepared using a fluid carrier for use as a mouthwash, wherein the compound in the fluid carrier is applied orally and swished and expectorated or swallowed. Pharmaceutically compatible binding agents, and/or adjuvant materials can be included as part of the composition. The tablets, pills, capsules, troches and the like can contain any of the following ingredients, or compounds of a similar nature: a binder such as microcrystalline cellulose, gum tragacanth or gelatin; an excipient such as starch or lactose, a disintegrating agent such as alginic acid, Primogel, or corn starch; a lubricant such as magnesium stearate or Sterotes; a glidant such as colloidal silicon dioxide; a sweetening agent such as sucrose or saccharin; or a flavoring agent such as peppermint, methyl salicylate, or orange flavoring.

For administration by inhalation, the compounds are delivered in the form of an aerosol spray from pressured container or dispenser which contains a suitable propellant, e.g., a gas such as carbon dioxide, or a nebulizer.

Systemic administration can also be by transmucosal or transdermal means. For transmucosal or transdermal administration, penetrants appropriate to the barrier to be permeated are used in the formulation. Such penetrants are generally known in the art, and include, for example, for transmucosal administration, detergents, bile salts, and fusidic acid derivatives. Transmucosal administration can be accomplished through the use of nasal sprays or suppositories. For transdermal administration, the active compounds are formulated into ointments, salves, gels, or creams as generally known in the art.

The compounds can also be prepared in the form of suppositories (e.g., with conventional suppository bases such as cocoa butter and other glycerides) or retention enemas for rectal delivery.

In one embodiment, the active compounds are prepared with carriers that will protect the compound against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art. The materials can also be obtained commercially from Alza Corporation and Nova Pharmaceuticals, Inc. Liposomal suspensions (including liposomes targeted to infected cells with monoclonal antibodies to viral antigens) can also be used as pharmaceutically acceptable carriers. These can be prepared according to methods known to those skilled in the art, for example, as described in U.S. Pat. No. 4,522,811, incorporated fully herein by reference.

It is especially advantageous to formulate oral or parenteral compositions in dosage unit form for ease of administration and uniformity of dosage. Dosage unit form as used herein refers to physically discrete units suited as unitary dosages for the subject to be treated; each unit containing a predetermined quantity of active compound calculated to produce the desired therapeutic effect in association with the required pharmaceutical carrier. The specification for the dosage unit forms of the invention are dictated by and directly dependent on the unique characteristics of the active compound and the particular therapeutic effect to be achieved.

The pharmaceutical compositions can be included in a container, pack, or dispenser together with instructions for administration.

Assay Method

The starting material for assay of the invention may be DNA (e.g., genomic DNA, mitochondrial DNA) or RNA (e.g., mRNA, structural RNA). Preferably, the nucleic acid to be analyzed may comprise a portion of a particular gene or genetic locus in a patient's genomic DNA known to be involved in a pathological condition or syndrome. The nucleic acid used as starting material may be obtained from any cell source or body fluid. Methods for converting RNA into DNA, such as, for example, by the use of reverse transcriptase with oligo-dT or random primers are known. Non-limiting examples of cell sources available in clinical practice include blood cells, buccal cells, cervicovaginal cells, epithelial cells from urine, fetal cells, or any cells present in tissue obtained by biopsy including tumor cells. Body fluids include blood, urine, cerebrospinal fluid, and tissue exudates at the site of infection or inflammation. If desired, DNA is extracted from the cell source or body fluid using any of the numerous methods that are standard in the art. It will be understood that the particular method used to extract DNA will depend on the nature of the source.

The assay of the invention is directed to a method for detecting one or more sequence changes in a plurality of target nucleic acid sequences in a nucleic acid sample which may comprise four steps. Each of the steps is discussed in more detail below.

Step (a) Endonuclease Digestion of a DNA Sample

In step (a) endonuclease digestion is performed on a DNA sample to produce a plurality of DNA fragments. The endonuclease is chosen to specifically target and digest the wild-type 7G homopolymer sequence (GCCCCCCCAGC (SEQ ID NO: 1)) compared to the mutant 8G homopolymer sequence (GCCCCCCCCAGC (SEQ ID NO: 2)). The endonuclease is for example MwoI.

In one preferred embodiment the endonuclease digestion of step (a) is performed as follows:

a. Prepare MwoI restriction digestion mix for 96 samples as follows:

| Reagent | X1 Reaction (ul) | X110 Reactions (1 plate) (ul) |
|---|---|---|
| NEB Buffer #3 | 2.5 | 275 |
| MwoI (5 U/ul) | 1 | 110 |
| Water | 16.5 | 1,815 |
| DNA (20 ng/ul) | 5 | NA | b. Vortex digestion reaction well for 30 seconds and spin down
c. Begin digestion program
   "MUC1_Digest"
   60 Deg C.→16 Hours
   10 Deg C.→Forever
d. After 3 hours @ 60 Deg C., remove plate
   i. Spin down plate @ 3000 RMP for 1 min
   ii. Using fresh tips, add 1 ul MwoI (5 U/ul)
   iii. Seal and vortex plate well for 30 seconds and spin down
   iv. Return plate to cycler and continue with MUC1 Digest
e. After 16 hours @ 60 Deg C., remove plate
   i. Spin down plate @ 3000 RMP for 1 min
   ii. Using fresh tips, add 1 ul MwoI (5 U/ul)
   iii. Seal and vortex plate well for 30 seconds and spin down
   iv. Return plate to cycler and continue with MUC1 Digest
f. Return plate to 60 Deg C. for final 1 hour digestion and remove.

Step (b) PCR Amplification

In step (b) PCR is performed on the plurality of DNA fragments obtained from step (a) to enrich for insertion-containing fragments over wild-type background. The DNA fragments of step (a) are amplified using Tailed primers nested within the 60-bp VNTR repeat which will specifically amplify intact VNTR fragments. Primer sequences are: InterMuc_L (CTGGGAATCGCACCAGCGTGTGGC-CCCGGGCTCCACC (SEQ ID NO:4)) InterMuc_R (CGTGGATGAGGAGCCGCAGTGTCCGGGGCCGAG-GTGACA (SEQ ID NO:5)).

PCR amplification produces a plurality of amplified DNA fragments.

In a preferred embodiment the PCR amplification of step (b) is performed as follows:
   a. Prepare PCR master mix as follows:

| Reagent | X1 Reaction (ul) | X110 Reactions (1 plate) (ul) |
|---|---|---|
| Buffer Qiagen 10X | 2.5 | 275 |
| MgCl2 (25 mM) | 1 | 110 |
| dNTP Mix (10 mM) | 1.92 | 211.2 |
| Primer (InterMuc_L) (10 um) | 0.48 | 52.8 |
| Primer (InterMuc_R) (10 um) | 0.48 | 52.8 |
| HotStart Plus Taq (5 U/ul) | 0.16 | 17.6 |
| Total: | 6.54 | 719.4 | b. Array 6.5 ul PCR master mix to each well of a fresh 96-well skirted Eppendorf plate
   c. Transfer 18.5 ul of eluted/digested template to appropriate wells d. Seal and cortex plate well for 30 seconds
e. Begin PCR program on MJ Tetrad Cycler "MUC1_45 X"
  95° C.→5 min
  94° C.→30 sec
  67° C.→30 sec
  72° C.→1 min
  GoTo Step 2→44X
  72° C.→10 min
  10° C.→Forever
f. Remove plate and spin down at 3000 RPM for 1 min Step (c) Second Endonuclease Digestion In step (c) endonuclease digestion is performed on the plurality of amplified DNA fragments produced by step (b) to produce a second plurality of DNA fragments. As in step (a) the endonuclease is chosen to specifically target and digests the wild-type 7G homopolymer sequence (GCCCCCCCAGC (SEQ ID NO:1)) compared to the mutant 8G homopolymer sequence (GCCCCCCCCAGC (SEQ ID NO:2)). The endonuclease is for example MwoI.

In one preferred embodiment the endonuclease digestion of step (a) is performed as follows:

a. Prepare MwoI restriction digestion mix as follows:

| Reagent | X1 Reaction (ul) | X110 Reactions (1 plate) (ul) |
|---|---|---|
| NEB Buffer #3 | 2.5 | 275 |
| MwoI (5 U/ul) | 1 | 110 |
| Template | 21.5 | N/A | b. Transfer 21.5 ul clean/eluted PCR product to new 96 well skirted Eppendorf plate
c. Array 3.5 ul MwoI mix to each well
d. Vortex digestion reaction well for 30 seconds and spin down
e. Begin digestion program
  "MUC1_Digest"
  60 Deg C.→16 Hours
  10 Deg C.→Forever
f. After 3 hours @ 60 Deg C., remove plate
  i. Spin down plate @ 3000 RMP for 1 min
  ii. Using fresh tips, add 1 ul MwoI (5 U/ul)
  iii. Seal and vortex plate well for 30 seconds and spin down
  iv. Return plate to cycler and continue with MUC1 Digest
g. After 16 hours @ 60 Deg C., remove plate
  i. Spin down plate @ 3000 RMP for 1 min
  ii. Using fresh tips, add 1 ul MwoI (5 U/ul)
  iii. Seal and vortex plate well for 30 seconds and spin down
  iv. Return plate to cycler and continue with MUC1 Digest
h. Return plate to 60 Deg C. for final 1 hour digestion and remove
i. Spin down plate at 3000 RPM for 1 min Step (d) Probe Extension In step (d) a probe extension reaction is performed in the second plurality of DNA fragments obtained from step (c). The probe is designed to specifically bind upstream of the cytosine insertion. The probe extension is performed using a high fidelity DNA polymerase and a nucleotide termination mix containing dATP, ddCTP and ddGTP The probe extension reaction produces a plurality of reaction products. For example the probe is a 19 bp probe having the sequence of CGGGCTCCACCGCCCCCCC (SEQ ID NO:3).

In a preferred embodiment the probe extension is preformed as follows:

a. Prepare extension master mix as follows

| Reagent | X1 Reaction (ul) | X110 Reactions (1 plate) (ul) |
|---|---|---|
| Buffer Qiagen 10X | 0.9 | 99 |
| MgCl2 (25 mM) | 0.24 | 26.4 |
| SAP Buffer | 1.7 | 187 |
| Term Mix (ddG, ddC, dA) (10 mM each) | 0.22 | 24.2 |
| Probe_13 (SEQ ID NO: 3) (10 uM) | 0.6 | 66 |
| ThermoSequenase (32 U/ul) | 0.02 | 2.2 |
| Water | 1.16 | 127.6 |
| Total | 4.84 | 532.4 | b. Array 4.84 ul of TermMix/Buffer to appropriate wells of a 384 well Eppendorf plate.
c. Transfer 5.16 ul of eluted template to mix containing wells
d. Seal plate, vortex well and spin down.
e. Place plate on ABI Viper cycler and run program: "HME-Ext"
  94° C.→2 min
  94° C.→5 sec
  52° C.→5 sec
  72° C.→5 sec
  GoTo Step 2→54X
  72° C.→7 min
  4° C.→Forever Step (e) Detection of the Mutant 8G Homopolymer Sequence In step (e) the presence of the mutant 8G homopolymer sequence is detected. The mutant 8G homopolymer sequence is detected by any method known in the art. As the wildtype and mutant homopolymer are of different size, size exclusion chromatography is particular suited for detection of the mutant 8G homopolymer sequence. For example the mutant 8G homopolymer sequence is detected using mass spectroscopy such as MALDI-TOF mass-spectrometry using the Sequenom MassArray platform. Spectra are assessed for the presence of peaks corresponding to the mutant extension-product (CGGGCTCCACCGCCCCCCC (SEQ ID NO:6)) at 5,904.83 daltons) and the wild-type extension-product (CGGGCTCCACCGCCCCCCAG (SEQ ID NO:7)) at 6258.06 daltons). Optionally prior to steps (b), (c) and/or (d) a purification step is performed by any method know in the art.

Although the present invention and its advantages have been described in detail, it should be understood that various changes, substitutions and alterations can be made herein without departing from the spirit and scope of the invention as defined in the appended claims.

The present invention will be further illustrated in the following Examples which are given for illustration purposes only and are not intended to limit the invention in any way.

EXAMPLES

Example 1

General Methods

Family Collection and Phenotyping

Families with MCKD1 share the following characteristics: absent or low grade proteinuria with bland urinary sediments; slowly progressive kidney dysfunction; absence of causative findings on renal ultrasound; and absence of other associated signs or symptoms of systemic disease. Hypertension tended to occur only after the onset of chronic kidney failure.

Given these clinical characteristics, the only quantifiable relevant phenotype for analysis was estimated glomerular filtration rate (GFR). Often serum creatinine is used to measure kidney function, as serum creatinine levels are reciprocally related to glomerular filtration rate. However, serum creatinine levels are also affected by other factors, including protein intake and muscle mass, making it an inaccurate renal function marker in people with preservation of 70%-100% of normal kidney function. The MDRD formula estimates kidney function based on race, gender, age, and serum creatinine Unfortunately, this formula is also inaccurate for patients with 70%-100% of normal kidney function. To further complicate matters, kidney function normally decreases with age, with some individuals experiencing significant loss of function—this is especially the case in African Americans and Native Americans.

Therefore age and GFR were the considering factors in arriving at the clinical diagnoses. Analysis of individuals of less than 18 years of age was not included, even though affected individuals under 18 could have a normal GFR. Individuals with significantly abnormal kidney function for their age were considered affected. Individuals were considered unaffected if kidney function was normal or if they were older and still had relatively preserved kidney function. In most of the families, affected individuals initiated renal replacement therapy (started dialysis) between 40 and 60 years of age.

Accordingly, individuals were considered affected if they required renal replacement therapy, had biopsy-proven interstitial kidney disease, or had an estimated GFR ≥2 standard deviations below the mean, adjusted for age and race. Individuals were considered to be unaffected if they were greater than 25 years of age and their estimated GFR was considered significantly higher than expected for affected family members. Approximately one-third of family members were excluded from initial genetic analysis due to indeterminate renal phenotypes. Medical records were reviewed and peripheral venous blood samples were obtained for DNA isolation and laboratory determinations.

Linkage and Copy Number Variant (CNV) Analysis

Family members were genotyped on the Affymetrix 6.0 platform using a standard analysis pipeline involving strict quality control of the raw data, rendering of highly informative subsets of markers appropriate for linkage mapping, confirmation of reported familial relationships, and further filtering of Mendelian inheritance errors and other likely genotyping errors.

Whole Affymetrix arrays with genotype call rates <88% were excluded from analysis, as were samples which yielded low OD measurements (indicating poor sample performance during laboratory steps). Further, markers were excluded for which probe sequences showed excess genomic homology or potential for significant G-quartet formation (those probe sequences for which either allele contained at least three consecutive G's).

Linkage mapping was performed using the Merlin package under a rare autosomal-dominant model (Abecasis, G. R., Cherny, S. S., Cookson, W. O. & Cardon, L. R. *Nat. Genet.* 30, 97-101 (2002)). Marker maps typically contained ~5,700 markers. Particularly large pedigrees (>24 bit complexity) were divided into branches where required by computational constraints; the consistency of the alleles carried on the segregating risk haplotype was confirmed across branches.

The boundaries of the linked region were refined by searching all well-typed markers—including many that were dropped solely to eliminate markers in LD (linkage disequilibrium) from the linkage calculations—for instances where affected members within the same pedigree shared no alleles IBD, or identical by descent (by virtue of being homozygous for opposite alleles—for example, one having genotype AA and another CC). Such markers necessarily lie outside the critical linkage interval.

LD-independent marker maps were separately created for each pedigree/branch, choosing single, well-typed, informative markers from LD-defined bins of SNPs based on phased, population-specific HapMap data (hapmap.org, release 22). Markers which showed no-call rates >10% or any Mendelian inheritance errors within a pedigree/branch were excluded from specific pedigree/branch analyses. Additionally, markers were required to be spaced at least 0.1 cM apart according to published sex-averaged recombination positions (affymetrix.com).

All expected intra-pedigree relationships were confirmed from pairwise IBD estimates using PLINK software[1] and similarly derived marker sets; however, markers for PLINK were selected agnostic to their being polymorphic within a pedigree/branch so as not to skew IBD calculations (Purcell, S. et al., *Am. J. Hum. Genet.* 81, 559-575 (2007)). Merlin software was used to remove any likely genotyping errors which did not violate Mendelian inheritance rules, and then to perform parametric linkage under a rare, autosomal-dominant model using population-specific allele frequencies (affymetrix.com). Linkage scores were combined across pedigrees/branches by summing LOD values, linearly interpolating scores between marker locations as required.

Affymetrix 6.0 intensity data were used by Birdsuite software to analyze copy-number variation (Korn, J. M. et al., *Nat. Genet.* 40, 1253-1260 (2008)).

Large-Scale Regional Sequencing

Whole-genome and Whole-exome Sequencing

Whole-genome and whole-exome ibraries were sequenced on either Illumina HiSeq 2000 or Illumina GAIIX with the use of 101-bp paired-end reads for whole-genome sequencing and 76-bp paired-end reads for whole-exome sequencing. The critical region contains more than 170 separate transcript annotations which may comprise over 75 RefSeq genes, amplicon-based resequencing of genic regions was initially not considered. Of the 12 sequenced individuals, whole-genome sequencing was performed on 11 of these individuals (~25-fold coverage on average), whole-exome sequencing on 11 individuals (~180-fold coding-sequence coverage on average).

For a subset of samples, starting with 3 μg of genomic DNA, library construction was performed as described by Fisher et al (Fisher, S. et al., *Genome Biol.* 12, R1 (2011)). Another subset of samples, however, was prepared using the Fisher et al. protocol with some slight modifications: initial genomic DNA input into shearing was reduced from 3 μg to 100 ng in 50 μL of solution.

Exomes were captured using the Agilent SureSelect v2. For a subset of whole-genome samples, size selection was performed using gel electrophoresis, with a target insert size of either 340 bp or 370 bp+/−10%. Multiple gel cuts were taken for libraries that required high sequencing coverage. For another subset of whole-genome samples, size selection was performed using Sage's Pippin Prep.

Following sample preparation, libraries were quantified using quantitative PCR (kit purchased from KAPA biosystems) with probes specific to the ends of the adapters. This assay was automated using Agilent's Bravo liquid handling platform. Based on qPCR quantification, libraries were normalized to 2 nM and then denatured using 0.1 N NaOH using Perkin-Elmer's MultiProbe liquid handling platform.

Cluster amplification of denatured templates was performed according to the manufacturer's protocol (Illumina) using either Genome Analyzer v3, Genome Analyzer v4, HiSeq 2000 v2, or HiSeq v3 cluster chemistry and flowcells. For a subset of samples, after cluster amplification, SYBR Green dye was added to all flowcell lanes, and a portion of each lane visualized using a light microscope, in order to confirm target cluster density. Flowcells were sequenced either on Genome Analyzer IIX using v3 or v4 Sequencing-by-Synthesis Kits, then analyzed using RTA v1.7.48; or on HiSeq 2000 using HiSeq 2000 v2 or v3 Sequencing-by-Synthesis Kits, then analyzed using RTA v1.10.15. or RTA v.1.12.4.2.

Custom Capture-array

A custom sequence-capture microarray was designed to perform target enrichment of chromosome 1 152-156 Mb (hg18), including the critical MCKD1-linked region. Of the 12 sequenced individuals, regional-capture sequencing was performed on 5 individuals (~220-fold coverage on average).

The four megabase region was tiled with probes using Nimblegen in-house repeat masking algorithm (Okou, D. T. et al., *Nat. Methods* 4, 907-909 (2007)). Each array contains 385,000 probes tiled with ~5 bp overlap, excluding the repetitive sequence. The probe set covered 70% of the 4-Mb target region, or 85% if 100 bp offset around probes is used.

For each sample Applicants fragmented 5 μg of genomic DNA, using a water bath sonicator (Bioruptor, Diagenode) on high power. The sonication program was cyclical, 30 seconds on and 30 seconds off for a total of 15 minutes to obtain fragments of 200 to 800 bp. The size of the fragments was evaluated on DNA1000 chips (Agilent 2100 Bioanalyzer, Agilent). Library preparation was performed using the Illumina Paired end kit according to the manufacturer's protocol. In short: DNA fragments were blunt ended with T4 and Klenow polymerases and T4 polynucleotide kinase with 10 mM dNTP. A 3' adenosine overhang was added using Klenow exo fragment and 1 mM dATP followed by ligation of Illumina sequencing adapters with the Quick ligase. The agarose gel electrophoresis size-selection step was omitted. Ligated fragments were enriched using 11-15 cycles of linker mediated (LM) PCR using a high-fidelity polymerase (Phusion, Finnzymes). 1 μg of cleaned PCR product was hybridized on the Roche Nimblegen Sequence Capture array following the manufacturer's protocol. After 3 days of hybridization, slides were washed and the enriched DNA was eluted. Eluted DNA was amplified with 14-18 cycles of LM-PCR, cleaned with QIAquick PCR purification kit (Qiagen), and quantified. Sequence capture efficiency was verified using real-time PCR amplification of three primer sets within the target region and three primer sets outside of the target region. Amplification of primer sets inside and outside the target region was compared using both sequence capture enriched DNA and the pre-capture DNA. An eight-to-ten fold difference in rt-PCR amplification was deemed to be successful enrichment.

Sequence Analysis

Sequence data was processed with Picard (http://picard.sourceforge.net/) and BWA for mapping reads (DePristo, M. A. et al., *Nat. Genet.* 43, 491-498 (2011); Li, H. & Durbin, R., *Bioinformatics* 26, 589-595 (2010)). SNPs and small indels were called using GATK, which utilizes base quality-score recalibration and local realignment at known indels (DePristo, M. A. et al., *Nat. Genet.* 43, 491-498 (2011); McKenna, A. et al., *Genome Res.* 20, 1297-1303 (2010)). The analyzed variable sites were restricted to those that pass GATK standard filters to eliminate events with strand-bias, low quality for the depth of sequencing achieved, homopolymer runs, and SNPs near indels.

Any non-reference allele present in both affected individuals of any pedigree and with a population frequency ≤1% (because rare, dominantly inherited, highly penetrant disease mutations should be present in control populations at very low frequency) were considered in the search for pathogenic MCKD1 mutation candidates. Non-coding regions were analyzed similarly.

To discover potential structural variation at the chromosome-1 locus, Genome STRiP was run on the sequenced individuals and on a control population of 32 Finnish genomes sequenced at low coverage by the 1000 Genomes Project (A map of human genome variation from population-scale sequencing. *Nature* 467, 1061-1073 (2010)).

Genome STRiP was run on both with the default parameters and also with relaxed parameter settings to attempt to increase sensitivity. In normal use, Genome STRiP looks only for signatures of large deletions indicated by unusual spacing or orientation of read pairs. For this application, Applicants additionally enabled Genome STRiP to perform read pair clustering across all possible read pair orientations to generate a set of 2,208 loci that might potentially contain some form of structural variation.

The evidence for each potential SV locus was reviewed, looking for evidence of structural rearrangement that was inherited and segregated with disease but was not found at appreciable frequency in the Finnish control samples or in other published data sets (1000 Genomes, Database of Genomic Variants).

All loci that passed initial screening manually using IGV was reviewed (Robinson, J. T. et al., *Nat. Biotechnol.* 29, 24-26 (2011)). Although evidence was found for a number of structural polymorphisms (as would be expected in any population of this size), none met the criteria expected for causal mutations.

MUC1-VNTR Screening, Sequencing, and Assembly

For selected individuals, gel-purified long-range-PCR products were cloned containing the full-length VNTR. Allele sizes derived from Southern blots and long-range PCR, together with known haplotype sharing between individuals in the same pedigree, in most cases permitted the identification of which MUG1 VNTR allele was part of the segregating risk haplotype (FIGS. 2*b* and *c*). In a few cases, the sizes of the risk and non-risk VNTR allele were nearly the same, precluding physical separation of the two alleles prior to molecular cloning. Using transposon hopping and capillary sequencing, Applicants then sequenced clones from each allele.

MUC1-VNTR Screening

Southern Blot Analysis

Genomic DNA (5-8 µg) was digested with 100 u HinfI (NEB). Digests were run on a 0.8% agarose gel, transferred to a BrightStar Plus Nylon membrane (Ambion) and hybridized overnight at 65° C. to a quadruply biotinylated synthetic 100mer oligonucleotide probe/52-Bio/CAGCCCACGGT-GTCACCTCGGCCCCGGACACCAGGCCGGC-CCCGGGC/iBiodT/CCACCGCCCCCCCAGCCCACG-GTGTCACC/iBiodT/CGGCCCCGGACACCAGGCCGGC (SEQ ID NO: 8) (IDT) present at 2 ng/ml in SuperHyb hybridization solution (Ambion) supplemented with 100 µg/ml sonicated salmon sperm DNA (Stratagene). After a final high-stringency wash at 65° C. in 0.2×SSC and 0.1% SDS, membrane-bound biotin was detected by a BrightStar BioDetect kit (Ambion).

Long-range PCR

The long-range PCR protocol was adapted from Fowler et al. (Fowler, J. C., Teixeira, A. S., Vinall, L. E. & Swallow, D. M., *Hum. Genet.* 113, 473-479 (2003)). Briefly, 7-µL PCR reactions contained 15 or 30 ng genomic DNA, 1.75 pmol of forward (GGAGAAAAGGAGACTTCGGCTAC-CCAG (SEQ ID NO:9)) and reverse (GCCGTTGTGCAC-CAGAGTAGAAGCTGA (SEQ ID NO:10)) primers, 5% DMSO, 625 µM of each dNTP, 1× reaction buffer with 3 mM $MgCl_2$, and 0.25 u DyNAzyme EXT DNA polymerase (Finnzymes). Thermocycling on GeneAmp 9700 instruments (ABI) was as follows: initial denaturation (90 s at 96° C.); 22 or 27 cycles (40 s at 96° C., 30 s at 65° C., 6 min at 68° C.) and final extension (10 min at 68° C.).

Targeted Sequencing of MUC1 VNTR (Cloning and Sanger Sequencing)

PCR reactions were run on 0.8% agarose gels. Bona fide full-length PCR products were excised, cleaned-up by Qia-Quick gel-extraction kits (Qiagen) and TOPO-TA cloned in pCR-4-TOPO vector in TOP10 cells (Invitrogen). After electroporation, kanamycin-resistant transformants (typically 8 clones per gel-purified PCR product) were analyzed by EcoRI digestion and long-range PCR (see above). Bona fide full-length plasmid clones, typically 2×2 clones for each allele in a given individual (2 independent PCR reactions, 2 clones each, typically 8 clones per individual) were subjected to in vitro transposition with EZ-Tn5 <TET-1> (Epicentre). For each clone, 384 triple-resistant (50 µg/ml Ampicillin+50 µg/ml Kanamycin+10 µg/ml Tetracycline) EC100 TransforMAX (Epicentre) transformants were robotically picked, grown up, miniprepped and sequenced with TET-1 FP-1(GGGTGCGCATGATCCTCTAGAGT(SEQ ID NO:11)) and TET-1 RP-1 (TAAATTGCACTGAAATCTA-GAAATA(SEQ ID NO:12)) primers. Sequencing reactions (5 µL) contained 0.75 µL 5× sequencing buffer, 0.4 µL BigDye Terminator v3.1, 0.1 µL dGTP BigDye Terminator v3.0 (all ABI), 3.5% DMSO, 1.8 pmol sequencing primer and 1.5 µL miniprepped plasmid. Sequencing reactions were thermocycled as follows: initial denaturation (1 min at 96° C.) then 40 cycles (30 s at 96° C., 15 s at 50° C., 4 min at 60° C.). Extension products were cleaned up by ethanol precipitation and run on 3730×1 DNA Analyzers (ABI).

Sequence Assembly

The exceptionally repetitive nature of the region, as well as the presence in the read data of both PCR errors and sequencing errors (exacerbated by the extreme GC content of the repeat), required a special assembly method that could distinguish bona fide genomic differences from errors. The method included three key conceptual components:

(1) The ability to distinguish between base calls supported by multiple reads from only a single clone, and those base calls supported by multiple clones.

(2) Sensitive error detection in stacks of reads determined to belong to the same genomic region as the result of an initial, less sensitive round of error correction.

(3) Allele construction by gluing reads together along long, perfect overlaps. Because of the repetitive sequence content, not all assemblies were complete or unique. Instead, some assembly frameworks suggested multiple possible resolutions across areas of ambiguity, forming entire/full networks of possible solutions for a particular allele.

The steps performed were:

1. Combining transposon pairs. The two reads of a pair were merged if Applicants could find an eight-base perfect overlap between them at the expected position on the reads. Otherwise, the two reads were used as input to the next step but not joined. At this stage Applicants also trimmed off read tails having low quality scores and removed vector sequence.

2. Error correction. Applicants developed a special error correction algorithm to account for PCR errors in a clone.

(a) Applicants found all L-mers in the reads, L=21, discarding those for which the quality of the middle base was below 30. Applicants then associated a count to the L-mer, namely the total number of instances in the reads, minus those in reads from the clone having the most instances. If the L-mer had a reduced count of at least two, Applicants called it good.

(b) Now again traverse the reads, looking at all L-mers that are not good. Consider the three possible L-mers obtained by changing the middle base. Suppose that only one of these is good, and that its reduced count is at least five. Then Applicants made a 'recommendation' that the middle base be changed.

(c) Traverse the recommendations. Carry them out, except in cases where two are within L/2 of each other. Set the quality score of changed bases to zero.

(d) Now being a second phase of error correction by aligning the reads to each other, using only alignments for which the sum of the two longest perfect match lengths was at least 500.

(e) For a given read, edit it, using the stack of reads aligned to it.

3. Joining error corrected reads. Reads were formed into a graph by gluing them together along a minimum overlap of K=544. Applicants then deleted all material in the graph that could not be found on a path from the first PCR primer to the second. Finally, Applicants simplified the graph to reflect known limitations on the size of the PCR product.

MUC1 Genotyping Protocol

Genomic DNA was first over-digested using restriction endonuclease MwoI which selectively cleaves the wild-type sequence (GCCCCCCCAGC (SEQ ID NO:1)), while leaving intact fragments containing the +C insertion (GCCCCCCC*C*AGC (SEQ ID NO:2), wherein the '*' designates the C insertion). Tailed primers nested within the 60-bp repeat were then used to PCR amplify the remaining intact VNTR fragments, thus enriching for insertion-containing fragments over wild-type background. PCR products were then re-digested with MwoI for a second round of enrichment. A 20-bp probe was then designed just upstream of the insertion site, and probe extension was performed using a high fidelity DNA polymerase and a nucleotide termination mix containing dATP, ddCTP and ddGTP. Following probe extension, reaction products were separated and sized by MALDI-TOF mass-spectrometry using the Sequenom MassArray platform. Spectra were then assessed for the presence of peaks corresponding to the mutant extension-product (at 5,904.83 daltons) and the wild-type extension-product (at 6258.06 daltons).

Restriction Digestion 100 ug of genomic DNA was digested in a 25 ul reaction volume for 16 hours using 5 units of MwoI restriction endonuclease (New England Biolabs) with supplemental additions of 5 units of enzyme at hours 3 and 15.

Digestion reactions were then cleaned using 50 ul AmPure beads according to manufacturers protocol (Agencourt, Beverly, Mass.) and digested DNA was eluted in 20 of nuclease free water.

InterMuc PCR Amplification

Remaining intact VNTR fragments were PCR amplified using 1× HotStart buffer, 1 mM, 0.8 mM dNTPs, 0.8 units of HotStart Taq Plus (Qiagen) and 0.2 uM forward and reverse primers (Forward_Primer: 5'-CTGGGAATCGCAC-CAGCGTGTGGCCCCGGGCTCCACC(SEQ ID NO:13)), Reverse Primer: 5'-CGTGGATGAGGAGccGCAGTGTC-CGGGGCCGAGGTGACA(SEQ ID NO:14)) in a 25 ul reaction volume. PCR cycling conditions were: one hold at 95° C. for 5 min; 45 cycles of 94° C. for 30 sec, 67° C. for 30 sec, 72° C. for 1 min; followed by one hold at 72° C. for 10 min. PCR reactions were cleaned using 50 ul AmPure beads according to manufacturers protocol (Agencourt, Beverly, Mass.) and amplicons were eluted in 23 ul nuclease free water.

Second MwoI Restriction Digestion

A second round of MwoI digestion was performed again for 16 hours with 5 units of enzyme added at hours 0, 3 and 15. Digestion reactions were cleaned using 50 ul AmPure beads according to manufacturers protocol (Agencourt, Beverly, Mass.) and product was eluted in 6.2 ul of nuclease water.

Extension Reaction using Probe_13

Using 5.2 ul of the digested eluate as template, probe extension was performed using 1× HotStart buffer, 0.6 mM 1.7 ul SAP buffer (Sequenom, San Diego, Calif.), 0.2 mM each of nucleotides ddGTP, ddCTP and dATP; 0.7 units of Thermo Sequenase DNA polymerase (Amersham) and 0.6 uM of extension probe (5'-CGGGCTCCACCGCCCCCCC (SEQ ID NO:3)) in a 10 ul reaction volume. Probe extension was performed on a 384-well ABI GeneAMP 9700 and cycling conditions were; one hold at 94° C. for 2 min 55 cycles of 94° C. for 5 sec, 52° C. for 5 sec, 72° C. for 5 sec; followed by one hold at 72° C. for 7 min. Reactions were then de-salted using the addition of a cation-exchange resin and ~7 nl of purified extension reaction was spotted onto a SpectroChip (Sequenom) containing matrix 3-hydroxipicoloinic acid. Arrayed reactions were then analyzed by matrix-assisted laser desorbtion/ionization-time of flight (MALDI-TOF) on a Compact mass spectrometer (Sequenom/Bruker)

Assay results were clear enough to assign genotypes based on simple inspection of X-Y scatterplots depicting log-transformed wild-type and mutant intensities ($\log_{10}$ (1.0+peak height)). Samples showing log-transformed intensities <0.25 for both alleles were considered failed assays. Similarly, results from whole-genome-amplification samples or samples with low DNA concentrations were typically considered unreliable and discarded.

Example 2

Linkage Analysis Identifies a 2-Mb Critical Region Spanning 1q21.3 and 1q22

Figure 3:
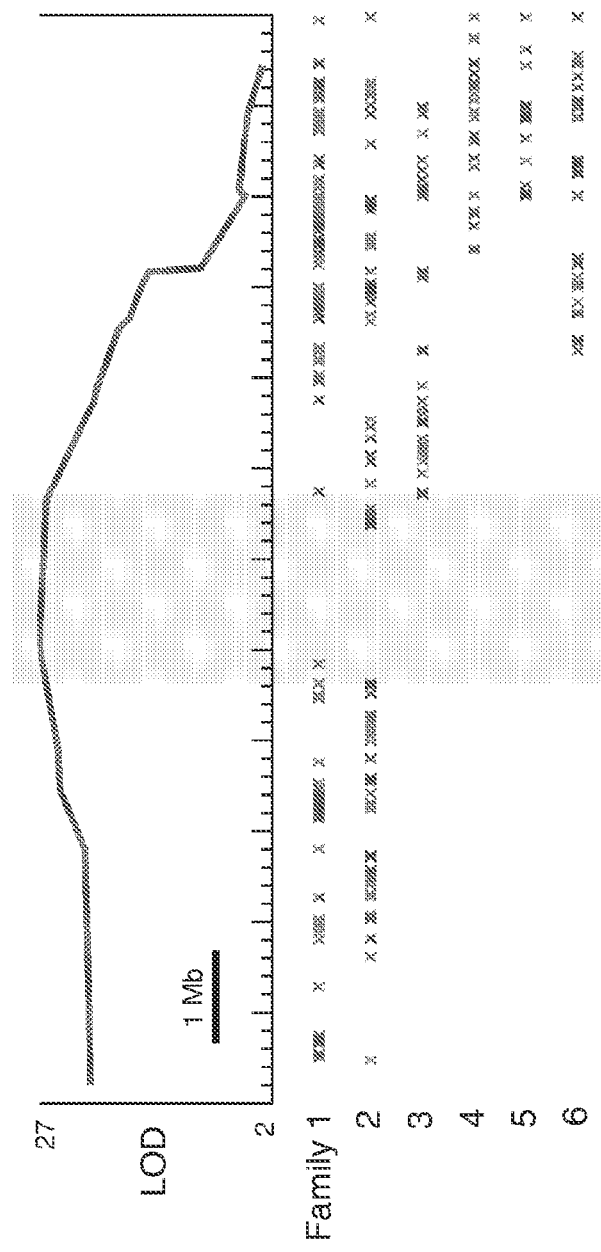
FIG. 3. Linkage of six MCKD1 families to chromosome 1. LOD curve shows the combined linkage-score of six MCKD1 pedigrees across 12 Mb of chromosome 1, with the peak score well above the threshold of 3.6 for genome-wide significance (Lander, E. & Kruglyak, L., *Nat. Genet.* 11, 241-247 (1995)). Red X's mark the locations of opposite-allele homozygous genotype calls between affected members within each pedigree and highlight regions where affected individuals de facto share no alleles IBD, thereby delineating genomic segments unlikely to harbor causal variation. The shaded region (hg19:chr1:154,370,020-156,439,000) was considered most likely to contain any causal mutations.

To define a precise region containing the MCKD1 gene, Applicants focused on six multiplex MCKD pedigrees showing autosomal-dominant inheritance of kidney disease with bland urinary sediment. These families had been screened to be free of mutations in the genes UMOD and REN, associated with similar disease phenotypes, and several had previously demonstrated linkage to the reported MCKD1 localization on chromosome 1q (Kiser, R. L. et al., Am. J. Kidney Dis. 44, 611-617 (2004); Kimmel, R. J. et al., Am J Psychiatry 162, 1972-1974 (2005); Bleyer, A. J., Zivná, M. & Kmoch, S., Nephron Clin Pract 118, c31-36 (2011); Beck, B. B. et al., Am. J. Kidney Dis. 58, 821-825 (2011; Kenya, P. R., Asal, N. R., Pederson, J. A. & Lindeman, R. D., South. Med. J. 70, 1049-1051 (1977)). Linkage mapping was performed under a model of autosomal dominant inheritance, and in all families the phenotype showed perfect co-segregation with a single region of chromosome 1, yielding a combined LOD score of 27.0 (FIG. 3); the next most significant region of the genome showed a cumulative LOD of only 2.2. The perfect co-segregation suggested little, if any, phenocopy. The MCKD1 critical region spanned 2.07 Mb (hg19 chr1:154,370,020-156,439,000), bounded on each side by recombination breakpoints in two different pedigrees.

Applicants examined the critical interval for evidence of copy-number variation, but found only two common CNPs, neither of which segregated with disease. Applicants then searched the critical region for evidence of an extended haplotype shared across any of the families, suggestive of a founder mutation. Examining the longest stretches of identity within pairwise comparisons of the pedigrees' phased risk-haplotypes, Applicants found no obvious ancestral haplotype shared by a significant fraction of the families (and which was more extensive than the LD in the general population). This result suggested that the families carried independently occurring mutations, a finding consistent with the families' diverse ancestry, including European-American, African-American and Native-American descent.

Example 3

Large-Scale Sequencing Reveals No Candidates for Causal Variation

To search for mutations, Applicants employed several parallel large-scale sequencing strategies in order to get full regional sequence coverage, with an emphasis on coding sequence. Applicants selected two affected individuals from each pedigree for sequencing, chosen, where possible, to share only a single haplotype (the risk haplotype) across the linkage region. Applicants focused first on the analysis of protein-coding sequences. Applicants found only two rare, non-silent, coding point variants (SNPs or small indels) shared by both of the affected individuals in any pedigree, with each of the two variants in a different gene and each in a different pedigree. The finding of two such variants is consistent with the expected background rate, given the examination of 75 genes, six haploid genomes and the presence of ~100 such rare coding variants in a typical genome (A map of human genome variation from population-scale sequencing. Nature 467, 1061-1073 (2010)). In the context of perfect segregation of the risk haplotype within families, the near-complete coverage of the coding bases in the linked region and the experience with other Mendelian diseases, Applicants had expected to find a gene harboring rare coding variants in multiple families. To Applicants' dismay, Applicants found no such evidence.

Applicants next examined the non-coding regions, but found no regional clustering of segregating rare variants.

Applicants then searched for any large structural variation (hundreds of bases or larger) such as deletions, insertions, duplications and inversions (relative to the reference genome). All variants identified in this manner either failed to segregate with disease or were found at appreciable levels in control populations.

At this point, Applicants concluded that the causal mutation(s) in MCKD1 were either located in a subregion that was recalcitrant to sequencing or represented a novel mutational mechanism. The certainty of the linkage results and the recombination boundaries gave us the confidence to undertake a thorough examination of these possibilities.

Example 4

Critical Region Scanned for Coding VNTR-Expansion Candidates

Applicants considered the possibility that MCKD1 might be due to expansions in a coding VNTR sequence, because recurrent mutations at coding VNTRs have been documented as the cause of many genomic disorders and because massively parallel sequencing data might not readily reveal such an expansion (Gemayel, R., Vinces, M. D., Legendre, M. & Verstrepen, K. J., *Annu. Rev. Genet.* 44, 445-477 (2010)).

Applicants used SERV (Sequence-based Estimation of minisatellite and microsatellite Repeat Variability)[17] to identify highly variable tandem repeats (VNTRs) in or overlapping with coding regions in the disease-linked interval (Legendre, M., Pochet, N., Pak, T. & Verstrepen, K. J., *Genome Res.* 17, 1787-1796 (2007)). Such repeat regions were found in five genes: KCNN3, EFNA3, ASH1L, MEF2D and MUC1. Candidate VNTRs in the first four genes were found either to be non-polymorphic or to show no notable expansion in affected individuals (relative to family members not sharing the risk haplotype and to CEPH family samples), based on direct assays of length by PCR.

The VNTR most strongly predicted to be polymorphic was in MUC1, and although often annotated as non-coding, the evidence is clear that the VNTR is fully contained within coding sequence (Brayman, M., Thathiah, A. & Carson, D. D., *Reprod. Biol. Endocrinol.* 2, 4 (2004); Swallow, D. M. et al., *Nature* 328, 82-84 (1987); Levitin, F. et al., *J. Biol. Chem.* 280, 33374-33386 (2005)). MUC1 was of particular interest because it was the only gene in the critical region with highly enriched mRNA expression in the kidney, based on RNASeq data from an adult control individual (unrelated to this study). The MUC1 VNTR proved remarkably difficult to assay: it consists of a large repeat unit (60 bases) with very high GC-content (>80%) and many repeats (20-125 copies) (Home, A. W. et al., *Lancet* 357, 1336-1337 (2001); Fowler, J. C., Teixeira, A. S., Vinall, L. E. & Swallow, D. M., *Hum. Genet.* 113, 473-479 (2003)). Applicants ultimately assayed the VNTR by Southern blot and confirmed the results by performing long-range PCR (FIG. 2c). A Southern blot with genomic DNA digested by HinfI gave results consistent with published descriptions of the VNTR, with each measured chromosome carrying bands of size 3.5-5.5 kb, suggesting a range of 34-68 repeat units in Applicants' patient samples; however, the genome reference (hg19) predicts a band size of only 2.1 kb (<12 repeat units), far smaller than the published range or that observed in any of Applicants' samples, including controls (Fowler, J. C., Teixeira, A. S., Vinall, L. E. & Swallow, D. M., *Hum. Genet.* 113, 473-479 (2003)).

While the MUC1 VNTR was polymorphic in Applicants' families, Applicants found no evidence of unusual expansion on risk chromosomes.

Example 5

Targeted Sanger Sequencing of Muc1 Coding VNTR Reveals Insertion Variant in Affecteds At this point, Applicants were left with the possibility that MCKD1 might be caused by point mutations within the large, extremely GC-rich MUC1 coding VNTR, which was poorly represented in Applicants' sequence data: (i) it was excluded from whole-exome and regional-capture probes due to its low-complexity and extreme sequence composition and (ii) it was dramatically underrepresented in QC-filtered data, even in the whole-genome sequence, likely due to its GC-richness and homopolymer content. In addition, Applicants were concerned about the reliability of the human reference sequence in this region, and thus undertook to perform de novo assembly of the VNTR alleles of several affected individuals (FIG. 2b-d), using data generated by long-range PCR followed by cloning, transposon hopping, and capillary sequencing. For comparison, Applicants also cloned and Sanger sequenced the MUC1-VNTR alleles from a CEPH trio (Table 1 and FIG. 4).

Applicants found a number of point variants in the VNTR assemblies. With one exception, they either did not segregate with the risk haplotype or were present in the alleles of the CEPH trio and/or unaffected chromosomes. However, Applicants found one variant consistent with disease segregation: the insertion of a single C (relative to the coding strand of MUC1) within a stretch of seven C's occurring at positions 53-59 in a single copy of the canonical 60-mer repeat (FIG. 2e). In all six families, Applicants found the +C insertion in the assemblies of VNTR alleles, even when the assembly graph could not be fully and unambiguously resolved (Table 1). Moreover, the affected individuals for whom Applicants were able to separately sequence both alleles were found to have one allele with the mutation and one without the mutation. Finally, the four distinct parental alleles from the CEPH trio (which were separately and completely assembled) lacked this mutation. (FIG. 4 and Table 1)

TABLE 1

Summary of MUC1-VNTR assemblies.

| Family | ID | Affected | Relationship | Linkage sharing across VNTR | Linkage haplotypes across VNTR | VNTR size in bases | Edge count in VNTR assembly | +C found in sequence data | +C found by genotype assay |
|---|---|---|---|---|---|---|---|---|---|
| 1 | II-2 | Y | aunt/nephew | IBD1 | F1-a | 2,640 | 1 | N | Y |
| | | | | | F1-b (risk) | (4.8 kb) | 12 | Y | |

TABLE 1-continued

Summary of MUC1-VNTR assemblies.

| Family | ID | Affected | Relationship | Linkage sharing across VNTR | Linkage haplotypes across VNTR | VNTR size in bases | Edge count in VNTR assembly | +C found in sequence data | +C found by genotype assay |
|---|---|---|---|---|---|---|---|---|---|
| | III-5 | Y | | | F1-c | 2,700 | 1 | N | Y |
| | | | | | F1-b (risk) | (4.8 kb) | 50 | Y | |
| 2 | IV-5 | Y | second cousins | IBD1 | F2-a | 2,100 | 1 | N | Y |
| | | | | | F2-b (risk) | (4.1 kb) | 19 | Y | |
| | IV-3 | Y | | | F2-c | (2.2 kb) | 13 | N | Y |
| | | | | | F2-b (risk) | (4.1 kb) | 5 | Y | |
| 3[10] | III-13 | Y | full sibs | IBD1 | F3-a (risk) | (4.8 kb) | 13 | Y | Y |
| | | | | | F3-b | (4.8 kb) | n/s? | ? | |
| | III-16 | Y | | | F3-c | (4.0 kb) | 47 | N | Y |
| | | | | | F3-a (risk) | (4.8 kb) | 39 | Y | |
| 4 | V-3 | Y | first cousins once removed | IBD1 | F4-a (risk) | 2,641 | 1 | Y | Y |
| | | | | | F4-b | (4.3 kb) | n/a | ? | |
| | IV-2 | Y | | | F4-a (risk) | 2,641 | 1 | Y | Y |
| | | | | | F4-c | (4.5 kb) | n/a | ? | |
| 5[11] | IV-5 | Y | half first cousins | IBD1 | F5-a | 2,640 | 1 | N | Y |
| | | | | | F5-b (risk) | (4.7 kb) | 33 | Y | |
| | IV-1 | Y | | | F5-c | 4,680 | 1 | N | Y |
| | | | | | F5-b (presumed risk) | (4.7 kb) | n/s? | ? | |
| 6[12] | IV-3 | Y | first cousins | IBD0 | F6-a | 2,640 | 1 | N | Y |
| | | | | | F6-b (presumed risk) | 2,641 | 1 | Y | |
| | IV-4 | N | | | F6-c | 2,640 | 1 | N | N |
| | | | | | F6-d | (4.6 kb) | 12 | N | |
| CEPH | mom | N | | | CEPH-a | 2,400 | 1 | N | N |
| | | | | | CEPH-b | 2,940 | 1 | N | |
| | dad | N | | | CEPH-c | 2,580 | 1 | N | N |
| | | | | | CEPH-d | 4,320 | 1 | N | |
| | child | N | | | CEPH-a | 2,400 | 1 | N | N |
| | | | | | CEPH-d | 4,320 | 1 | N | |

Table 1. Knowledge of IBD sharing between/among sequenced individuals and the segregation of different phased SNP-marker haplotypes across the VNTR region were used to assign the sequenced MUC1 alleles to the different observed categorical linkage haplotypes, where possible. Furthermore, where able, Applicants have assigned VNTR alleles to a pedigree's risk haplotype. The reported size of each allele's assembly covers hg19 chr1 155,160,963 to 155,162,030 (inclusive). Numbers in parentheses are estimated sizes derived from long-range PCR gels in those cases where the allele was not assembled or did not assemble into a single unambiguous solution with an edge count of 1. Alleles with edge counts of "n/a" were not assembled, and alleles with edge counts of "n/s?" are believed to have not been assembled due to inadequate separation from the individual's other allele prior to molecular cloning.

Figure 6:
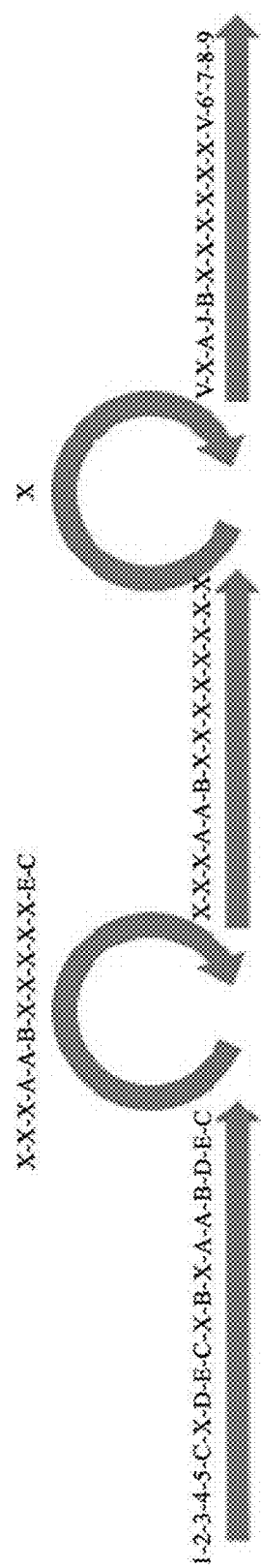
FIG. 6. Ambiguous assembly of a risk allele. For individual F2:IV-3's risk allele, the assembly of amplicon sequence data yielded a graph as shown, with an edge count of 5. The semantics of such a graph is that the true allele should be represented by some path through the graph from beginning to end. There are infinitely many paths through this particular graph, depending on how many times each loop is traversed, however almost all are inconsistent with the approximate amplicon size as measured from the long-range PCR gel (4.1 kb). Indeed Applicants reasoned that the only probable paths are those that traverse the first loop exactly 1 time, and the second loop between 5 and 7 times. This gives the same result as the assembly of the risk allele as depicted in FIG. 2 (c).

In families 2, 4, and 6, Applicants were able to identify precisely which individual 60-base repeat unit harbored the insertion and found it to be family-specific (the 5th, the 7th and the 16th 60-base repeat unit); in each case, the mutation is also carried in a slightly different local sequence context (FIG. 5 and FIG. 6). These findings, in addition to the different overall size of the VNTR for each of the three alleles, indicate that, although the six families all carry a +C insertion, the mutation appears to have arisen independently in each family.

Single-base insertions in a coding region cause a frame-shift that is typically followed soon thereafter by a novel stop codon. In contrast, no novel stop codon is encountered within the MUC1 VNTR owing to its high GC-content. The first novel stop codon is predicted to occur shortly beyond the VNTR terminus at hg19 position 155,160,870 (negative strand) (FIG. 2a), producing a mutant protein that contains many copies of a novel repeat sequence (obtained by shifted translation of the VNTR) but lacks the downstream SEA self-cleavage and transmembrane domain characteristic of the wild-type MUC1 precursor protein.

Example 6

Genotyping of MUC1 +C Insertion Confirms Association to MCKD1

Applicants' method for discovering the +C insertion (long-range PCR, cloning, transposon hopping, capillary sequencing, and regional assembly) was far too laborious to serve as a general assay for studying the event in larger numbers of individuals. Applicants therefore sought to devise a simple and robust genotyping assay. Importantly, Applicants needed an assay that could detect the presence of one additional C within a run of seven Cs, in exactly one copy (but in any copy) of ~100 nearly identical highly GC-rich 60-base repeats. Applicants therefore designed a probe-extension assay capable of distinguishing wild-type and mutant MUC1 VNTR repeat units, making use of MwoI (which selectively cleaves the wild-type sequence) to increase the stoichiometric ratio of mutant:wild-type repeat units.

Figure 7A:
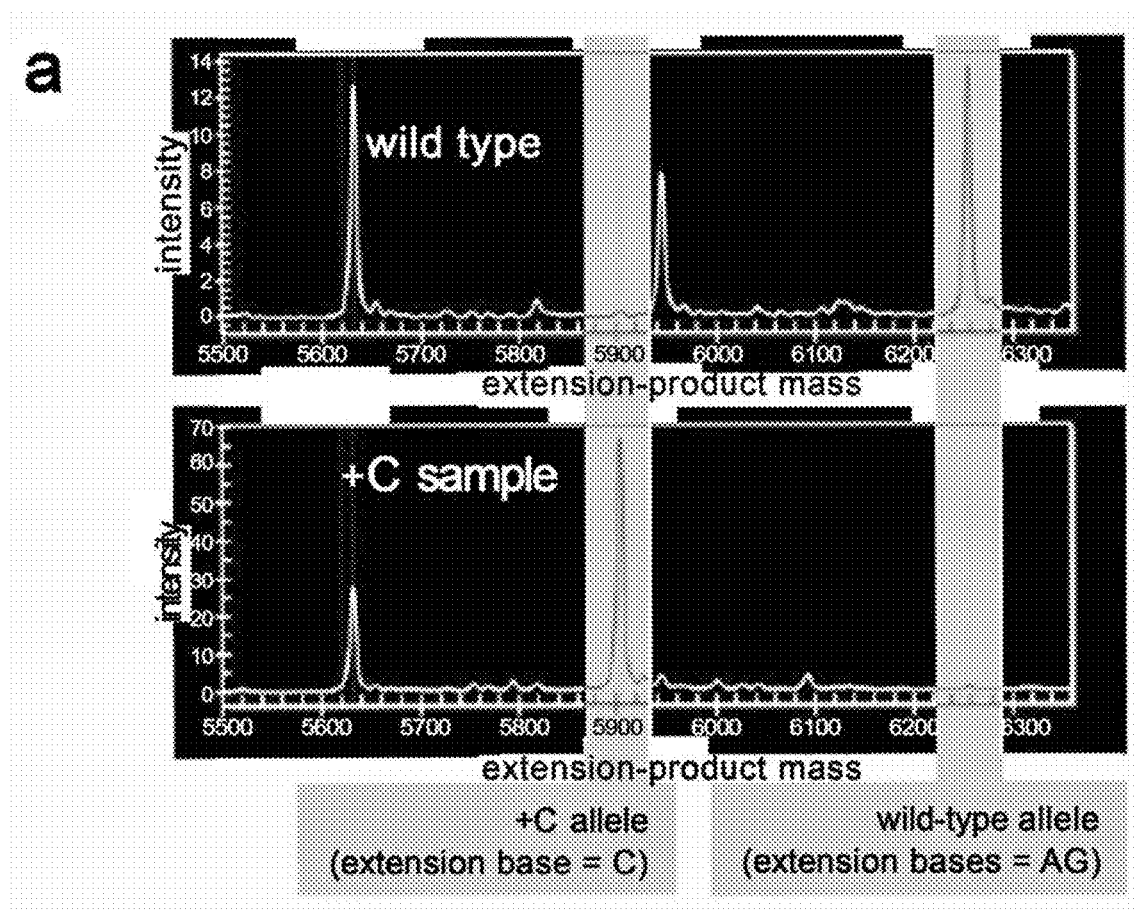
FIG. 7. Detection of MUC1 +C insertion by probe-extension (PE) assay. (a) Reference electropherograms for the MUC1-VNTR +C-insertion PE assay (see Supplementary Methods) performed on homozygous wild-type and heterozygote samples. (b) Allele-intensity scatterplot for large linkage family 2. X-axis values correspond to the detected intensity at the mass of the +C PE product, while Y-axis values reflect that of the wild-type extension product. Datum coloring reflects MCKD1 diagnosis: blue=unaffected (or HapMap samples), red=affected, white=unknown. Individuals known to carry the linkage-analysis risk haplotype are represented by a "+", while other family members are depicted as dots. (c) Allele-intensity scatterplot for all MCKD1 linkage families. Samples having log-transformed intensities below 0.25 for both alleles were excluded as failed assays. WGA and low DNA-concentration samples were also excluded for underperforming (d) Allele-intensity scatterplot for HapMap samples together with selected positive controls (MCKD1 individuals known to carry the insertion).
Figure 7B:
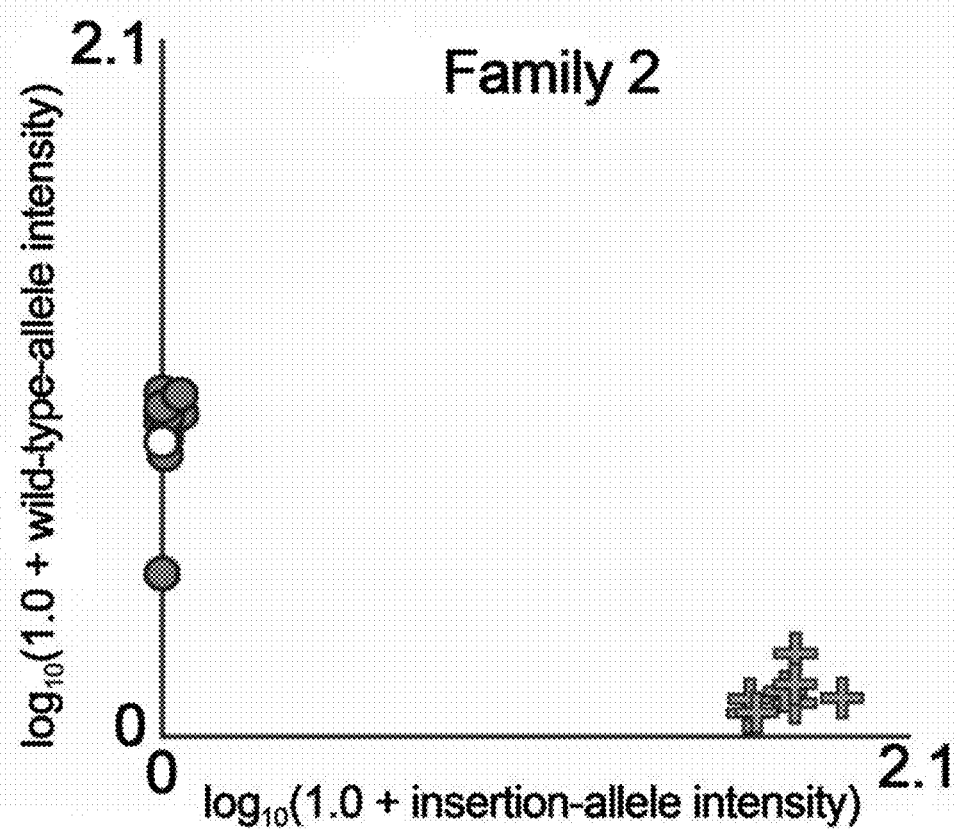
Figure 7C:
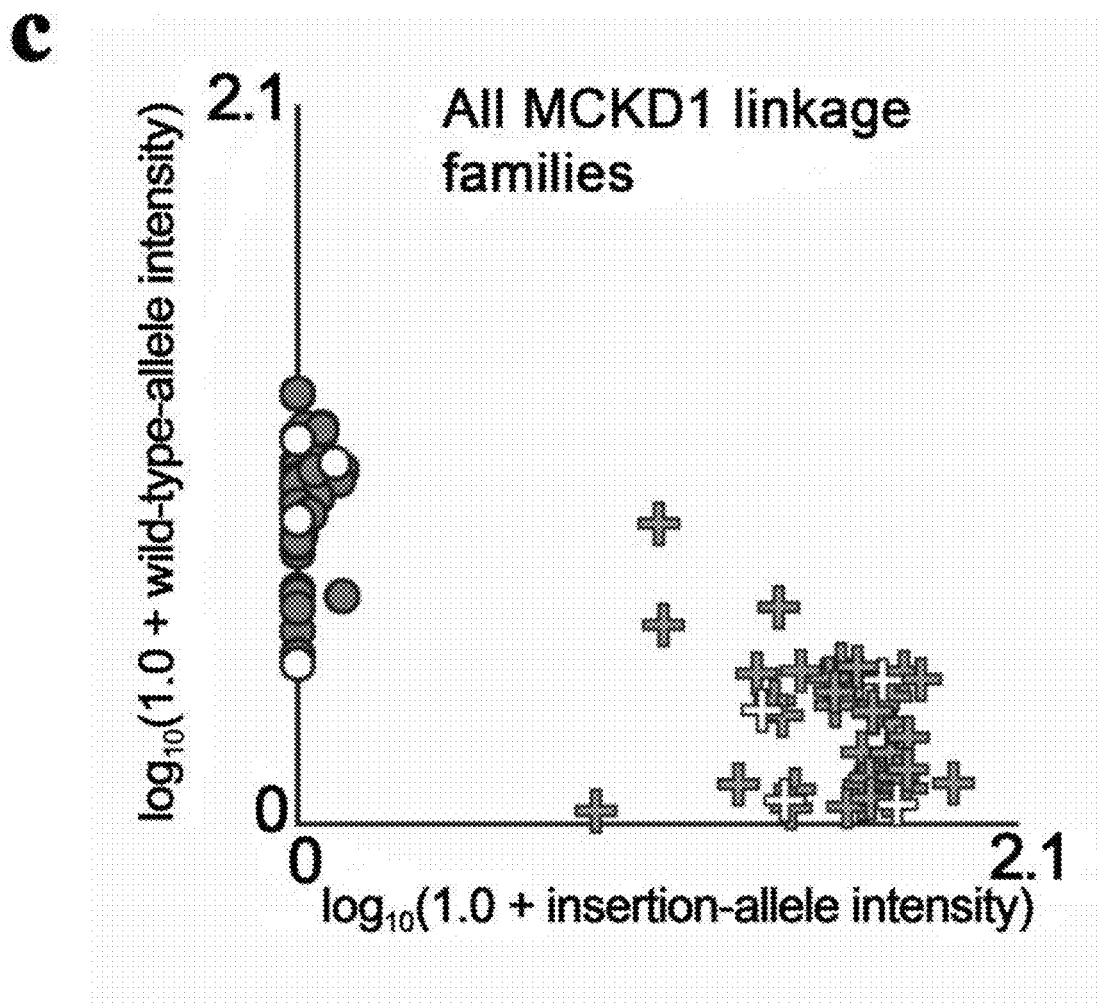
Figure 7D:
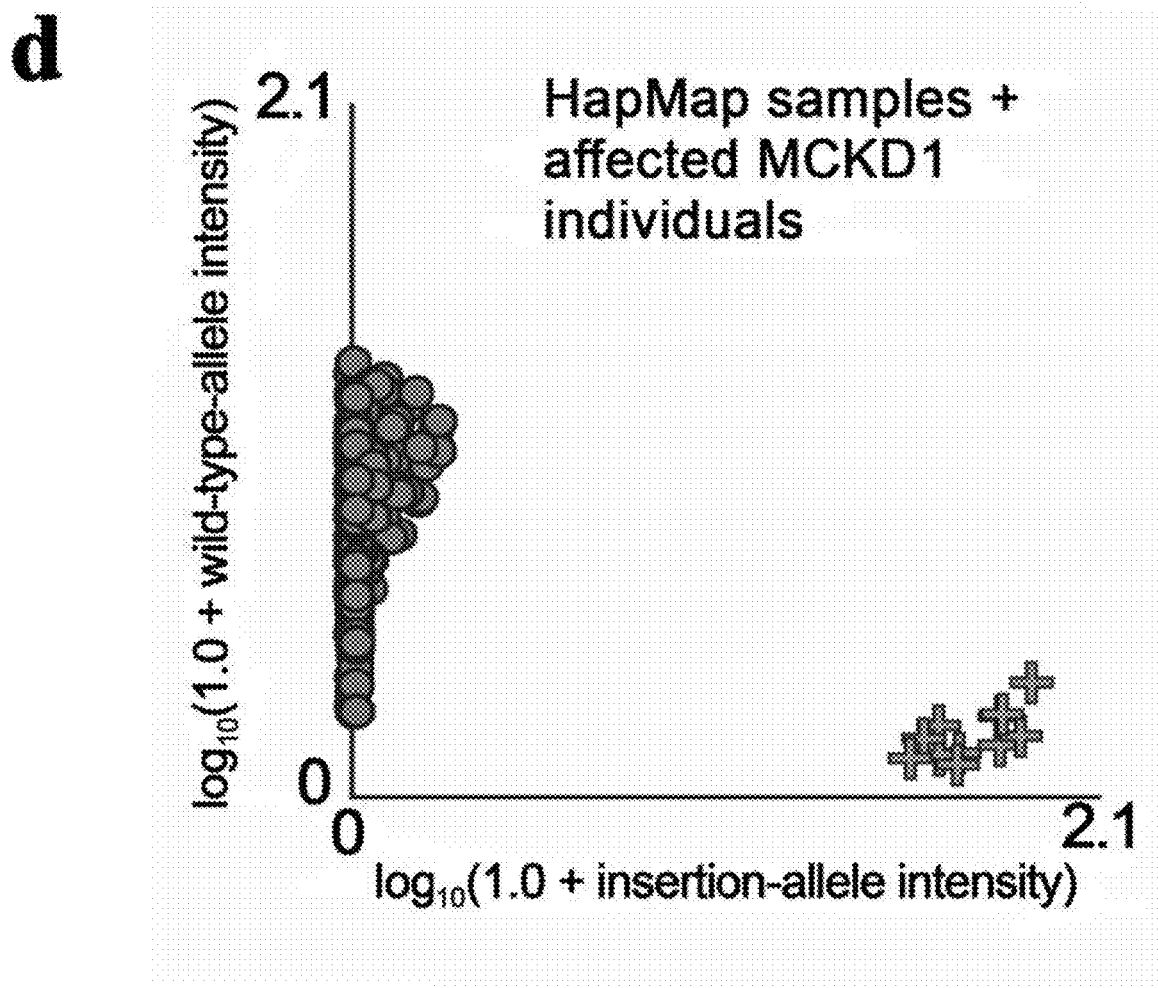

With this genotyping assay, Applicants studied all samples collected from the six MCKD1 families used for linkage analysis, including 62 phenotypically affected and 79 unaffected relatives (FIG. 7b-c). Additionally, Applicants genotyped over 500 control individuals from CEU, Japanese, Chinese, Yoruba and Tuscan HapMap3 populations (FIG. 7d). For each affected individual found by sequencing to carry a +C insertion, the genotyping assay confirmed the presence of a +C insertion, and full genotyping of all family members showed that the insertion segregated perfectly with each family's risk haplotype. None of the over 500 HapMap individuals showed evidence of a +C insertion.

The results indicate that a +C insertion likely occurred independently in 6 of 6 risk chromosomes but in none of >1,000 control chromosomes. As a statistical association, the significance of this observation can only be approximated, but it is clearly far less than the inverse of the number of bases in the genome. Furthermore, this observation is robust to population structure considerations since the mutations have arisen independently. Overall, the genotyping results provide strong evidence that the +C insertions are the high-penetrance genetic lesion that leads to development of MCKD1.

Having defined the causal mutation in the fully penetrant large families, Applicants sought to assess its role in sporadic cases and smaller families without definitive linkage information. Applicants examined both affected and unaffected individuals from 21 additional MCKD families screened to be negative for UMOD and REN mutations. In 12 of these families Applicants found the presence of a +C insertion consistent with being a fully penetrant cause of disease. The absence of insertions in nine of the families suggests that other MUC1 mutations and/or MCKD loci may yet remain undiscovered.

Example 7

Existence of MUC1-fs Confirmed in Kidneys of MCKD1 Patients

Figure 8:
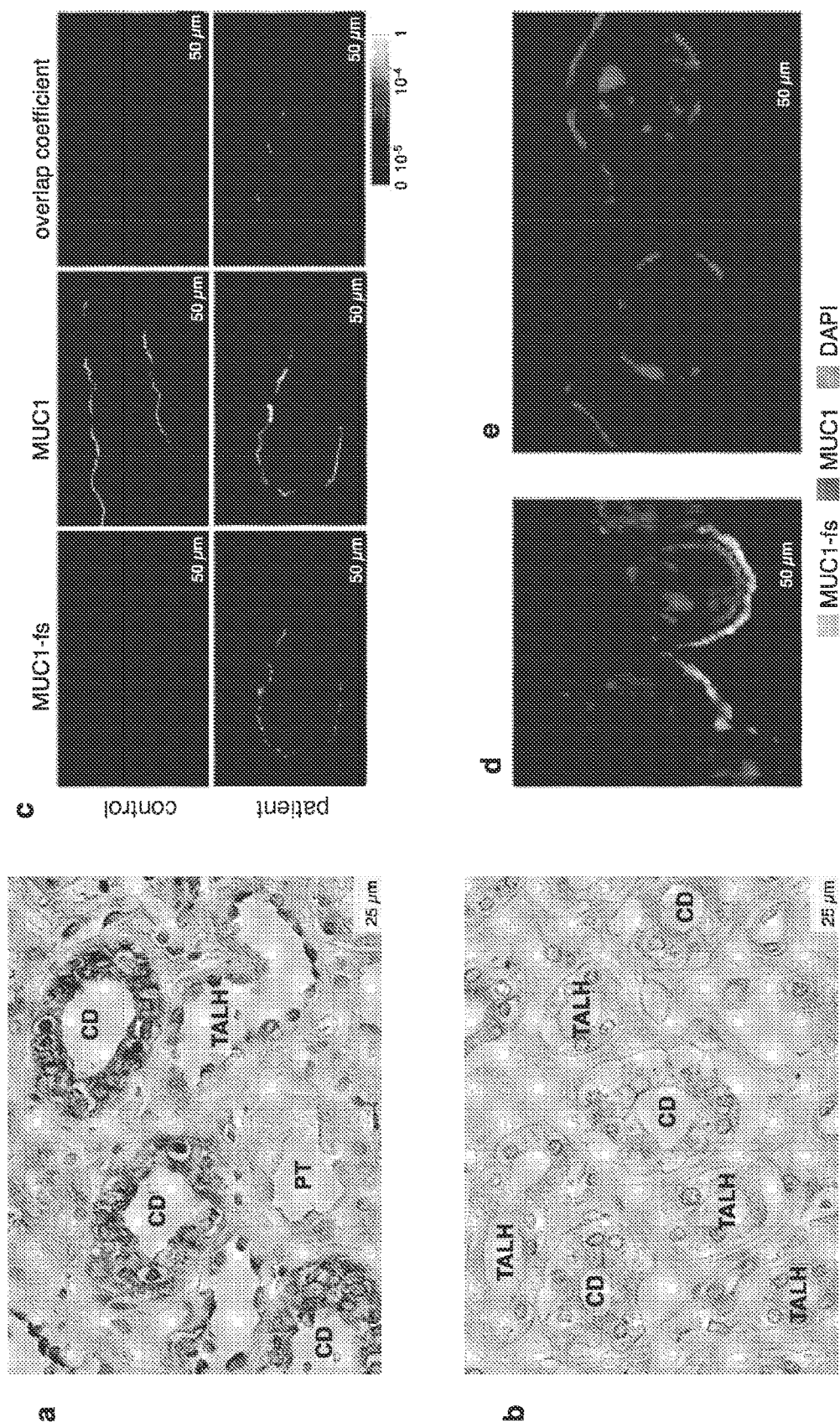
FIG. 8. Immunohistochemical and immunofluorescence studies of MUC1-fs protein. In MCKD1 patients, MUC1-fs is expressed and present in renal epithelial cells of Henle's loop, distal convoluted tubule, and collecting duct. (a) Strong intracellular staining of MUC1-fs protein in MCKD1 patient, and (b) absence of the specific staining in control; TALH—thick ascending limb of Henle's loop; CD—collecting duct; PT—proximal tubule. (c) Immunofluorescence analysis showing diffuse and/or fine granular intracellular and membrane staining of MUC1-fs protein, and its partial colocalization with wild-type MUC1 in collecting duct of MCKD1 patient. MUC1-fs staining is absent in control, and colocalization with wild-type MUC1 is therefore not detected. The values of fluorescent signal overlaps are transformed to a pseudo-color scale which is shown at right bottom in the corresponding lookup table. (d) Immunofluorescence analysis showing in detail different intracellular localizations and partial sub-membrane colocalization of MUC1-fs and wild-type MUC1 proteins in collecting duct of MCKD1 patient. Note otherwise specific staining of both forms in distinct membrane microdomains. (e) Absence of MUC1-fs staining and characteristic membrane localization of wild-type MUC1 in control.

Applicants next sought to detect expression of the predicted mutant protein, which Applicants refer to as MUC1-fs (frameshift). Using antibodies raised against a peptide synthesized based upon the predicted mutant VNTR sequence, Applicants found specific intracellular staining in epithelial cells of Henle's loop, distal tubule and collecting duct of MCKD1 patients (FIG. 8a), which was absent in control kidney (FIG. 8b). Co-staining of patient and control tissue additionally with antibodies against wild-type MUC1 demonstrated the specificity of the MUC1-fs antibodies for the mutant protein, with diffuse and/or fine granular intracellular localization of the MUC1-fs protein in patient kidney (FIG. 8c), and also patchy co-localization of MUC1-fs and wild-type MUC1 signals on the apical membrane of collecting duct epithelial cells (FIG. 8c, 8d). Detailed image analysis of patient tissue (FIG. 8d) compared to control tissue (FIG. 8e) detected no intracellular co-localization of MUC1-fs and wild-type MUC1 proteins in patient tissue, but revealed puncti of colocalization in distinct plasmalemmal subdomains.

Those skilled in the art will recognize, or be able to ascertain using no more than routine experimentation, numerous equivalents to the specific procedures described herein. Such equivalents are considered to be within the scope of the invention and are covered by the following claims. Various substitutions, alterations, and modifications may be made to the invention without departing from the spirit and scope of the invention as defined by the claims. Other aspects, advantages, and modifications are within the scope of the invention. The contents of all references, issued patents, and published patent applications cited throughout this application are hereby incorporated by reference. The appropriate components, processes, and methods of those patents, applications and other documents may be selected for the invention and embodiments thereof.

* * *

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. A method of treating a medullary cystic kidney disease type 1 (MCKD1) comprising detecting a point mutation resulting in insertion of a cytosine in the GC-rich variable number of tandem repeats (VNTR) sequence of the coding region of the mucin 1 gene (MUC-1) in a nucleic acid sample, wherein the presence of said point mutation indicates that the subject has or is predisposed to developing MCKD1;

said method comprising:
a. performing an endonuclease digestion on a nucleic acid sample; wherein said endonuclease selectively cleaves a wild-type MUC-1 nucleic acid sequence and not a mutant MUC-1 sequence having a cytosine insertion in the GC-rich variable number of tandem repeats (VNTR) region to produce a first plurality of nucleic acid fragments;
b. performing a PCR reaction on said first plurality of nucleic acid fragments to produce a plurality of amplified nucleic acid products;
c. performing a second endonuclease digestion on the plurality of amplified nucleic acid products, wherein said endonuclease selectively cleaves a wild-type MUC-1 nucleic acid sequence and not a mutant MUC-1 sequence having a cytosine insertion in the GC-rich variable number of tandem repeats (VNTR) region to produce a second plurality of nucleic acid fragments;
d. performing a probe extension reaction on said second plurality of nucleic acid fragments using a probe that specifically binds upstream of the cytosine insertion to produce a plurality of reaction products; and
e. measuring the mass or size of the reaction product and calculating the difference in mass or size from the wild type sequence, thereby determining a cytosine insertion in the GC-rich variable number of tandem repeats (VNTR) sequence of the coding region of the mucin 1 gene (MUC-1), and,
f. administering to a subject in need thereof a MUC-1 inhibitor, wherein the MUC-1 inhibitor is a MUC-1 nucleic acid, a MUC-1 specific short-interfering RNA, a MUC-1 specific ribozyme, a MUC-1 specific peptide inhibitor or a MUC-1 specific small molecule, wherein the MUC-1 inhibitor reduces MUC-1 production in a target cell.

2. The method of claim 1, wherein the endonuclease specifically cleaves a nucleic acid having the nucleic acid sequence GCCCCCCCAGC (SEQ ID NO: 1) and not a mutant sequence having the nucleic acid sequence GCCCCCCCCAGC (SEQ ID NO: 2).

3. The method of claim 1, wherein the endonuclease is Mwol.

4. The method of claim 1, wherein said probe comprises the nucleic acid sequence CGGGCTCCACCGCCCCCCC (SEQ ID NO:3).

5. The method of claim 1, wherein the detecting is performed by mass spectroscopy.

6. The method of claim 1, wherein the reaction product containing the cytosine insertion is about 5,904 daltons.

7. The method of claim 1, wherein a purification step is performed before step (b), (c) and or (d).

8. The method of claim 1, wherein the nucleic acid sample is DNA, RNA or cDNA.

9. A method of treating a medullary cystic kidney disease type 1 (MCKD 1) comprising
detecting a point mutation resulting in insertion of a cytosine in the GC-rich variable number of tandem repeats (VNTR) sequence of the coding region of the mucin 1 gene (MUC-1) in a nucleic acid sample, wherein the presence of said point mutation indicates that the subject has or is predisposed to developing MCKD1 and administering to a subject in need thereof a MUC-1 inhibitor, wherein the MUC-1 inhibitor is a MUC-1 nucleic acid, a MUC-1 specific short-interfering RNA, a MUC-1 specific ribozyme, a MUC-1 specific peptide inhibitor or a MUC-1 specific small molecule, wherein the MUC-1 inhibitor reduces MUC-1 production in a target cell.

10. The method of claim 9, wherein the detecting is performed by mass spectroscopy.

11. The method of claim 9, wherein the nucleic acid sample is DNA, RNA or cDNA.

12. The method of claim 9 further comprising amplifying a nucleic acid comprising the MUC-1 GC-rich variable number of tandem repeats (VNTR) region.

13. The method of claim 12 further comprising measuring the mass or size of the amplified nucleic acid and calculating the difference in mass or size from the wild type sequence, thereby determining a cytosine insertion in the GC-rich variable number of tandem repeats (VNTR) sequence of the coding region of the mucin 1 gene (MUC-1).

14. The method of claim 12, wherein the amplified nucleic acid containing the cytosine insertion is about 5,904 daltons.

15. The method of claim 1 or 9, wherein the MUC-1 inhibitor is an antisense MUC-1 nucleic acid, a MUC-1 specific short-interfering RNA, or a MUC-1 specific ribozyme.

16. The method of claim 1 or 9, wherein the MUC-1 inhibitor is Go-201 or Go-203.

17. The method of claim 1 or 9, wherein the MUC-1 inhibitor is a flavone having the structure

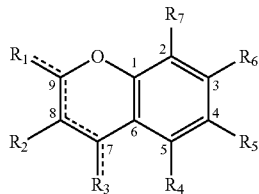

or a salt thereof, wherein $R_1$ is H, —OH, =O, substituted or unsubstituted alkyl ($C_{1-8}$), alkoxy($C_{1-8}$), haloalkyl($C_{1-8}$), substituted phenyl or unsubstituted phenyl, wherein if $R_1$ is =O, $C_7$-$C_8$ is a double bond;

$R_2$ is H, —OH, alkyl($C_{1-8}$), substituted phenyl, unsubstituted phenyl, phenyl, phenyl thiazole, imidazole, pyrazole or furan;

$R_3$ is H, —OH, =O, halogen, haloalkyl($C_{1-8}$), substituted or unsubstituted alkyl($C_{1-8}$), substituted phenyl or unsubstituted phenyl, wherein if $R_3$ is =O, $C_8$-$C_9$ is a double bond;

$R_4$ is H or —OH;

$R_5$ is H, —OH, substituted or unsubstituted alkyl($C_{1-8}$) or alkoxy($C_{1-8}$), or $OR_8$, wherein $R_8$ is alkyl($C_{1-8}$), an ester or an amide;

$R_6$ is H, —OH, substituted or unsubstituted alkyl($C_{1-8}$) or alkoxy($C_{1-8}$), or $OR_8$, wherein $R_8$ is alkyl($C_{1-8}$), an ester or an amide; and $R_7$ is H, —OH, or substituted or unsubstituted alkyl($C_{1-8}$), with the proviso that $R_1$ and $R_3$ cannot both be =O.

18. The method of claim 17, wherein the flavone is Morin, Apigenin, Kaempferol, Fisetin, PD98059, 7-(benzyloxy)-4-(trifluoromethyl)-2H-chromen-2-one or 7-[(3-oxobutan-2-yl)oxy]-4-phenyl-2H-chromen-2-one, or a salt thereof.

* * * * *